US011500400B2

(12) United States Patent
Jensen et al.

(10) Patent No.: US 11,500,400 B2
(45) Date of Patent: Nov. 15, 2022

(54) VALVE ACTUATION SYSTEMS AND RELATED METHODS

(71) Applicant: Fresenius Medical Care Holdings, Inc., Waltham, MA (US)

(72) Inventors: Lynn E. Jensen, Syracuse, UT (US); Philip Scott James, Orinda, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 8 days.

(21) Appl. No.: 16/519,077

(22) Filed: Jul. 23, 2019

(65) Prior Publication Data

US 2020/0033897 A1    Jan. 30, 2020

Related U.S. Application Data

(60) Provisional application No. 62/711,873, filed on Jul. 30, 2018.

(51) Int. Cl.
*G05D 7/06* (2006.01)
*A61M 1/16* (2006.01)
(Continued)

(52) U.S. Cl.
CPC .......... *G05D 7/0652* (2013.01); *A61M 1/166* (2014.02); *A61M 1/1656* (2013.01); *A61M 1/267* (2014.02); *A61M 1/3644* (2014.02); *F16K 11/20* (2013.01); *F16K 31/046* (2013.01); *A61M 2205/128* (2013.01); *A61M 2205/3303* (2013.01); *A61M 2205/3317* (2013.01); *A61M 2205/3331* (2013.01); *A61M 2205/3368* (2013.01); *A61M 2205/505* (2013.01)

(58) Field of Classification Search
CPC ..... Y10T 137/87708; Y10T 137/87048; F16K 11/20; F16K 31/042; F16K 31/043; F16K 31/046; F16K 31/047; A61M 2205/128; A61M 2205/3331
USPC .................................................. 251/292, 296
See application file for complete search history.

(56) References Cited

U.S. PATENT DOCUMENTS 2,530,581 A * 11/1950 Markis ................ F24D 19/1033
237/8 R
3,973,683 A * 8/1976 Keller ..................... B66C 13/48
414/591
(Continued)

FOREIGN PATENT DOCUMENTS

EP    1509261    3/2005
EP    2694127    2/2014
(Continued)

OTHER PUBLICATIONS

International Search Report and Written Opinion in Application No. PCT/US2019/043023, dated Oct. 8, 2019, 9 pages.
(Continued)

*Primary Examiner* — Seth W. MacKay-Smith
(74) *Attorney, Agent, or Firm* — Fish & Richardson P.C.

(57) ABSTRACT

In one aspect, a valve actuation system includes a drive unit including an actuator configured to engage and move multiple valves disposed within a fluid cassette to selectively open and close each valve of the multiple valves and a positioning frame disposed adjacent the fluid cassette and along which the drive unit can be moved in three dimensions to align the actuator with a selected valve of the multiple valves.

20 Claims, 35 Drawing Sheets

(51) Int. Cl.
*A61M 1/26* (2006.01)
*A61M 1/36* (2006.01)
*F16K 31/04* (2006.01)
*F16K 11/20* (2006.01)

(56) References Cited

U.S. PATENT DOCUMENTS

| | | | | |
|---|---|---|---|---|
| 4,001,556 | A * | 1/1977 | Folchi | B25J 13/081 |
| | | | | 700/258 |
| 4,229,136 | A * | 10/1980 | Panissidi | B25J 19/0012 |
| | | | | 414/673 |
| 4,274,802 | A * | 6/1981 | Inaba | B25J 9/101 |
| | | | | 414/591 |
| 4,363,585 | A * | 12/1982 | Keller | D01G 7/10 |
| | | | | 19/145.5 |
| 4,687,941 | A * | 8/1987 | Lasberg | B25J 21/02 |
| | | | | 250/506.1 |
| 5,111,997 | A * | 5/1992 | Ikuta | B05B 13/0452 |
| | | | | 239/227 |
| 5,540,668 | A | 7/1996 | Wilson, Jr. et al. | |
| 5,622,468 | A * | 4/1997 | Viollet | B66C 3/18 |
| | | | | 414/422 |
| 6,939,111 | B2 * | 9/2005 | Huitt | H05B 1/025 |
| | | | | 417/42 |
| 7,162,884 | B2 * | 1/2007 | Alles | F24F 3/0442 |
| | | | | 137/597 |
| 7,216,672 | B1 * | 5/2007 | Chen | F16K 11/20 |
| | | | | 137/883 |
| 8,555,926 | B2 * | 10/2013 | MacDuff | F24D 19/1015 |
| | | | | 137/883 |
| 9,827,361 | B2 * | 11/2017 | Pudil | A61M 1/1668 |
| 9,931,447 | B2 * | 4/2018 | Layser | F16K 5/18 |
| 10,058,694 | B2 * | 8/2018 | Norris | A61M 5/14224 |
| 11,085,552 | B2 | 8/2021 | Moss et al. | |
| 2003/0098270 | A1 | 5/2003 | Thompson | |
| 2004/0221904 | A1 | 11/2004 | Usher et al. | |
| 2005/0274658 | A1 | 12/2005 | Rosenbaum et al. | |
| 2007/0272311 | A1 | 11/2007 | Trocki et al. | |
| 2008/0172006 | A1 | 7/2008 | Hicks | |
| 2008/0214979 | A1 | 9/2008 | Brugger et al. | |
| 2010/0198129 | A1 | 8/2010 | Sternby et al. | |
| 2010/0312174 | A1 | 12/2010 | Hoffman | |
| 2014/0088482 | A1 | 3/2014 | Schlaeper et al. | |
| 2014/0097371 | A1 | 4/2014 | Huynh | |
| 2015/0343127 | A1 | 12/2015 | Childers et al. | |
| 2016/0008529 | A1 | 1/2016 | Hoffman | |
| 2016/0239025 | A1 * | 8/2016 | van der Merwe | F16K 27/0263 |
| 2017/0106131 | A1 | 4/2017 | Hornig | |
| 2017/0189598 | A1 | 7/2017 | Slade | |
| 2018/0229021 | A1 | 8/2018 | Donlon et al. | |
| 2019/0134289 | A1 | 5/2019 | Pudil et al. | |
| 2020/0030518 | A1 | 1/2020 | Brugger et al. | |
| 2020/0041021 | A1 | 2/2020 | Moss et al. | |
| 2020/0179674 | A1 | 6/2020 | Moss et al. | |
| 2020/0271232 | A1 | 8/2020 | Nakagami et al. | |
| 2021/0299340 | A1 | 9/2021 | Adams et al. | |
| 2021/0341073 | A1 | 11/2021 | Moss et al. | |

FOREIGN PATENT DOCUMENTS

| | | |
|---|---|---|
| GB | 2458572 | 9/2009 |
| WO | WO 2002/043859 | 6/2002 |
| WO | WO 2002/090671 | 11/2002 |
| WO | WO 03/099355 | 12/2003 |
| WO | WO 2009/064984 | 5/2009 |
| WO | WO 2011/017215 | 2/2011 |

OTHER PUBLICATIONS

PCT International Preliminary Report on Patentability in International Appln. No. PCT/US2019/043023, dated Feb. 11, 2021, 7 pages.
International Preliminary Report on Patentability in International Appln. No. PCT/US2019/042967, dated Feb. 11, 2021, 7 pages.
International Preliminary Report on Patentability in International Appln. No. PCT/US2019/044306, dated Feb. 11, 2021, 8 pages.
International Preliminary Report on Patentability in International Appln. No. PCT/US2019/057775, dated Jun. 17, 2021, 9 pages.
International Preliminary Report on Patentability in International Appln. No. PCT/US2020/044751, dated Feb. 17, 2022, 11 pages.
International Search Report and Written Opinion in International Appln. No. PCT/US2019/042967, dated Oct. 8, 2019, 11 pages.
International Search Report and Written Opinion in International Appln. No. PCT/US2019/044306, dated Oct. 24, 2019, 13 pages.
International Search Report and Written Opinion in International Appln. No. PCT/US2019/057775, dated Apr. 2, 2020, 17 pages.
International Search Report and Written Opinion in International Appln. No. PCT/US2020/044751, dated Nov. 4, 2020, 18 pages.
Invitation to Pay Additional Fees in International Application No. PCT/US2019/057775, dated Feb. 11, 2020, 11 pages.

* cited by examiner

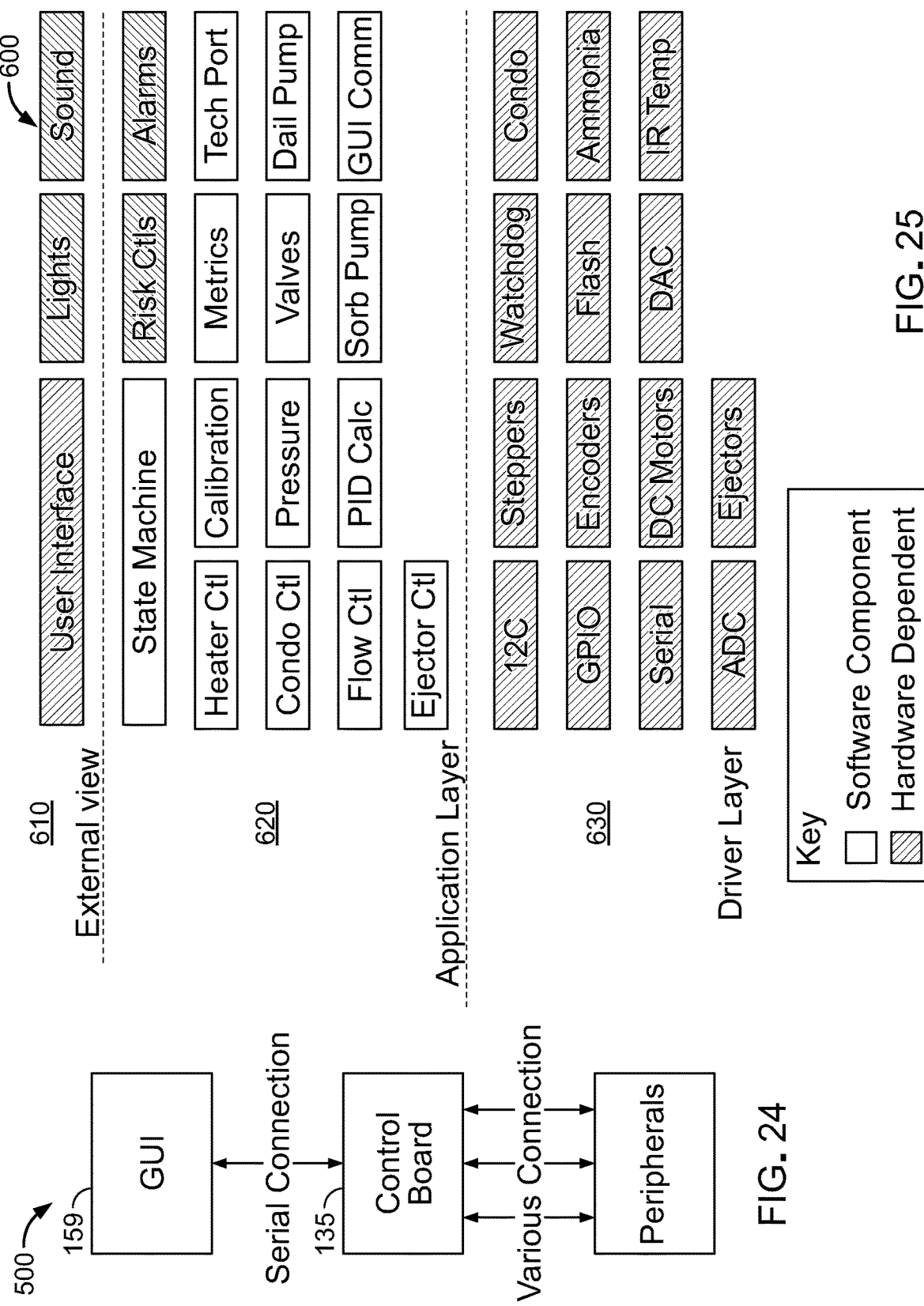

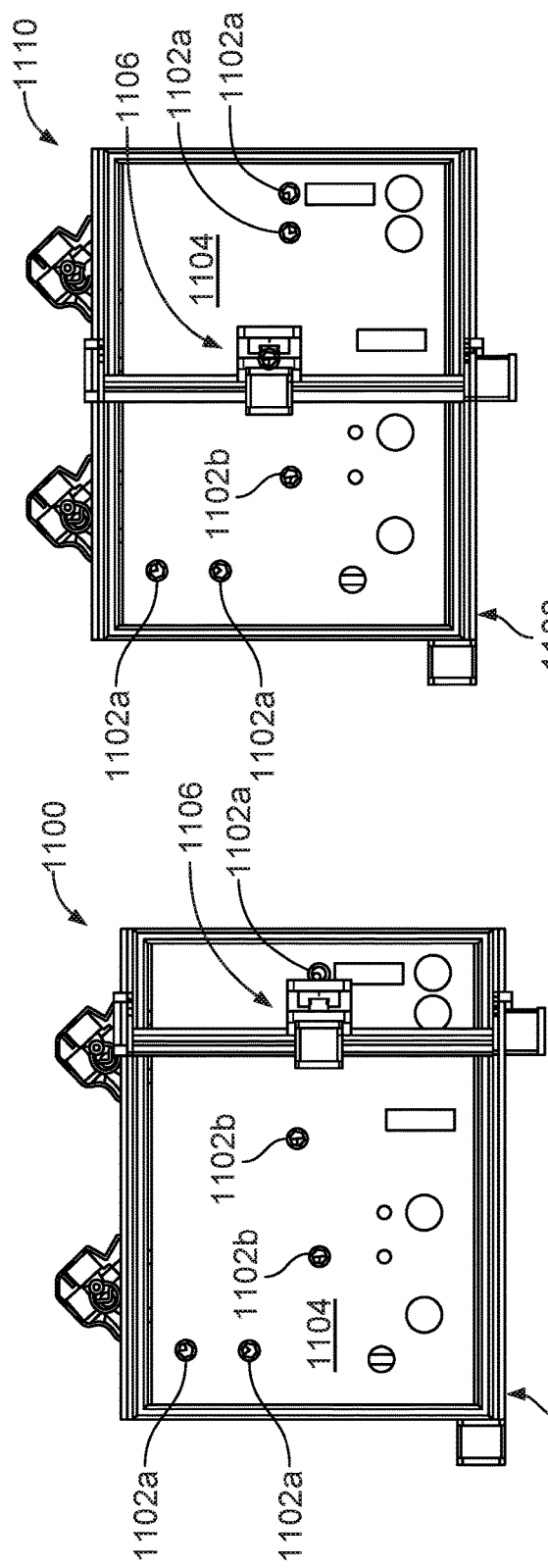
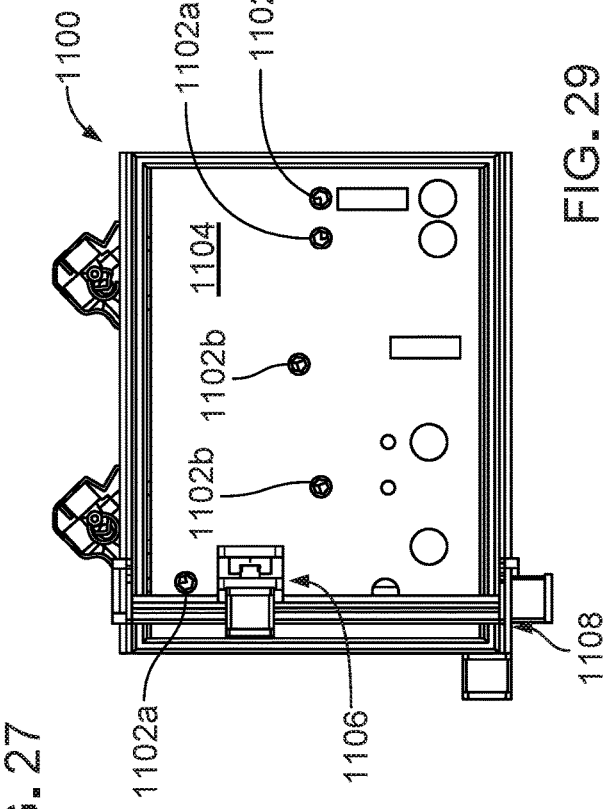

VALVE ACTUATION SYSTEMS AND RELATED METHODS

CROSS-REFERENCE TO RELATED APPLICATIONS

This application claims priority to U.S. Provisional Patent Application No. 62/711,873, filed on Jul. 30, 2018, the entire contents of which are incorporated herein by reference.

TECHNICAL FIELD

This disclosure relates to actuation systems for controlling valves of dialysis fluid cassettes.

BACKGROUND

Dialysis is a medical treatment that provides life-saving support to patients with insufficient renal function. The two principal dialysis methods are hemodialysis (HD) and peritoneal dialysis (PD). During HD, the patient's blood is passed through a dialyzer of a dialysis machine, while a dialysis solution (or, dialysate) is also passed through the dialyzer, generally in an opposite or countercurrent direction. A semi-permeable membrane within the dialyzer separates the blood from the dialysate and allows fluid exchanges to take place between the dialysate and the blood stream via diffusion, osmosis, and convective flow. These exchanges across the membrane result in the removal of waste products (e.g., such as solutes, like urea and creatinine) from the blood. These exchanges also help regulate the levels of other substances (e.g., sodium and water) in the blood. In this way, the dialyzer and dialysis machine act as an artificial kidney for cleansing the blood.

During PD, the patient's peritoneal cavity is periodically infused with dialysate. The membranous lining of the patient's peritoneum acts as a natural semi-permeable membrane that allows diffusion and osmosis exchanges to take place between the solution within the peritoneal cavity and the blood stream. Like HD, these exchanges across the patient's peritoneum result in the removal of waste products from the blood and help regulate the levels of other substances (e.g., sodium and water) in the blood.

Automated PD machines (e.g., PD cyclers) are designed to control the entire PD process so that it can be performed at home, usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other.

Various fluid paths within a dialysis system must be managed throughout a dialysis treatment via selective actuation of multiple dialysis fluid cassette valves.

SUMMARY

This disclosure relates to actuation systems for controlling valves of a cassette within a dialysis system.

In one aspect, a valve actuation system includes a drive unit including an actuator configured to engage and move multiple valves disposed within a fluid cassette to selectively open and close each valve of the multiple valves and a positioning frame disposed adjacent the fluid cassette and along which the drive unit can be moved in three dimensions to align the actuator with a selected valve of the multiple valves.

Embodiments may include one or more of the following features.

In some embodiments, the drive unit is carried by the positioning frame.

In some embodiments, the actuator is formed to mate with a complementary feature of each of the multiple valves.

In some embodiments, the actuator is configured to be controlled to apply a force to each valve of the multiple valves to rotate each valve of the multiple valves.

In some embodiments, the actuator is configured to open and close each valve of the multiple valves.

In some embodiments, the force is a rotational force.

In some embodiments, the positioning frame further includes a first linear rail, a second linear rail, and a third linear rail along which the drive unit can be moved linearly to align the actuator with the selected valve.

In some embodiments, the drive unit is configured to traverse the first, second, and third linear rails in a total time of up to about 0.5 seconds to about 2.0 seconds.

In some embodiments, the actuator is configured to open the selected valve to allow fluid to pass through the selected valve.

In some embodiments, the actuator is configured to close the selected valve to prevent fluid from passing through the selected valve.

In some embodiments, the actuator is configured to be controlled to apply a force to each valve of the multiple valves to move each valve of the multiple valves in a vertical direction.

In some embodiments, the actuator is configured to be controlled to push, pull, or slide each valve of the multiple valves.

In another aspect, a dialysis system includes a fluid cassette carrying multiple valves, a valve actuation system, and a control unit configured to control movements of the valve actuation system. The actuation system includes a drive unit including an actuator configured to engage and move the multiple valves disposed within the fluid cassette to selectively open and close each valve of the multiple valves, and a positioning frame disposed adjacent the fluid cassette and along which the drive unit can be moved in three dimensions to align the actuator with a selected valve of the multiple valves.

Embodiments may include one or more of the following features.

In some embodiments, the drive unit is carried by the positioning frame.

In some embodiments, the actuator is formed to mate with a complementary feature of each of the multiple valves.

In some embodiments, the actuator is configured to be controlled to apply a force to each valve of the multiple valves to rotate each valve of the multiple valves.

In some embodiments, the actuator is configured to open and close each valve of the multiple valves.

In some embodiments, the force is a rotational force.

In some embodiments, the positioning frame further includes a first linear rail, a second linear rail, and a third linear rail along which the drive unit can be moved linearly to align the actuator with the selected valve.

In some embodiments, the drive unit is configured to traverse the first, second, and third linear rails in a total time of up to about 0.5 seconds to about 2.0 seconds.

In some embodiments, the actuator is configured to open the selected valve to allow fluid to pass through the selected valve.

In some embodiments, the actuator is configured to close the selected valve to prevent fluid from passing through the selected valve.

In some embodiments, the actuator is configured to be controlled to apply a force to each valve of the multiple valves to move each valve of the multiple valves in a vertical direction.

In some embodiments, the actuator is configured to be controlled to push, pull, or slide each valve of the multiple valves.

Embodiments may provide one or more of the following advantages.

Owing to a capability of the actuation system to control multiple valves of a cassette, a design of the dialysis system including the actuation system can be simplified (e.g., including fewer components and/or requiring fewer control algorithms) relative to conventional dialysis systems that require a dedicated mechanism for actuating each valve of a cassette.

Other aspects, features, and advantages will be apparent from the description, the drawings, and the claims.

DESCRIPTION OF DRAWINGS

FIG. 24 provides a block diagram of a hardware system of the fluid conditioning system of FIG. 1.

FIG. 25 provides a block diagram of a software system of the fluid conditioning system of FIG. 1.

FIG. 27 is a top view of the actuation system of FIG. 26 showing a first configuration of the positioning frame.

FIG. 28 is a top view of the actuation system of FIG. 26 showing a second configuration of the positioning frame.

FIG. 29 is a top view of the actuation system of FIG. 26 showing a first configuration of the positioning frame.

DETAILED DESCRIPTION

Figure 1:
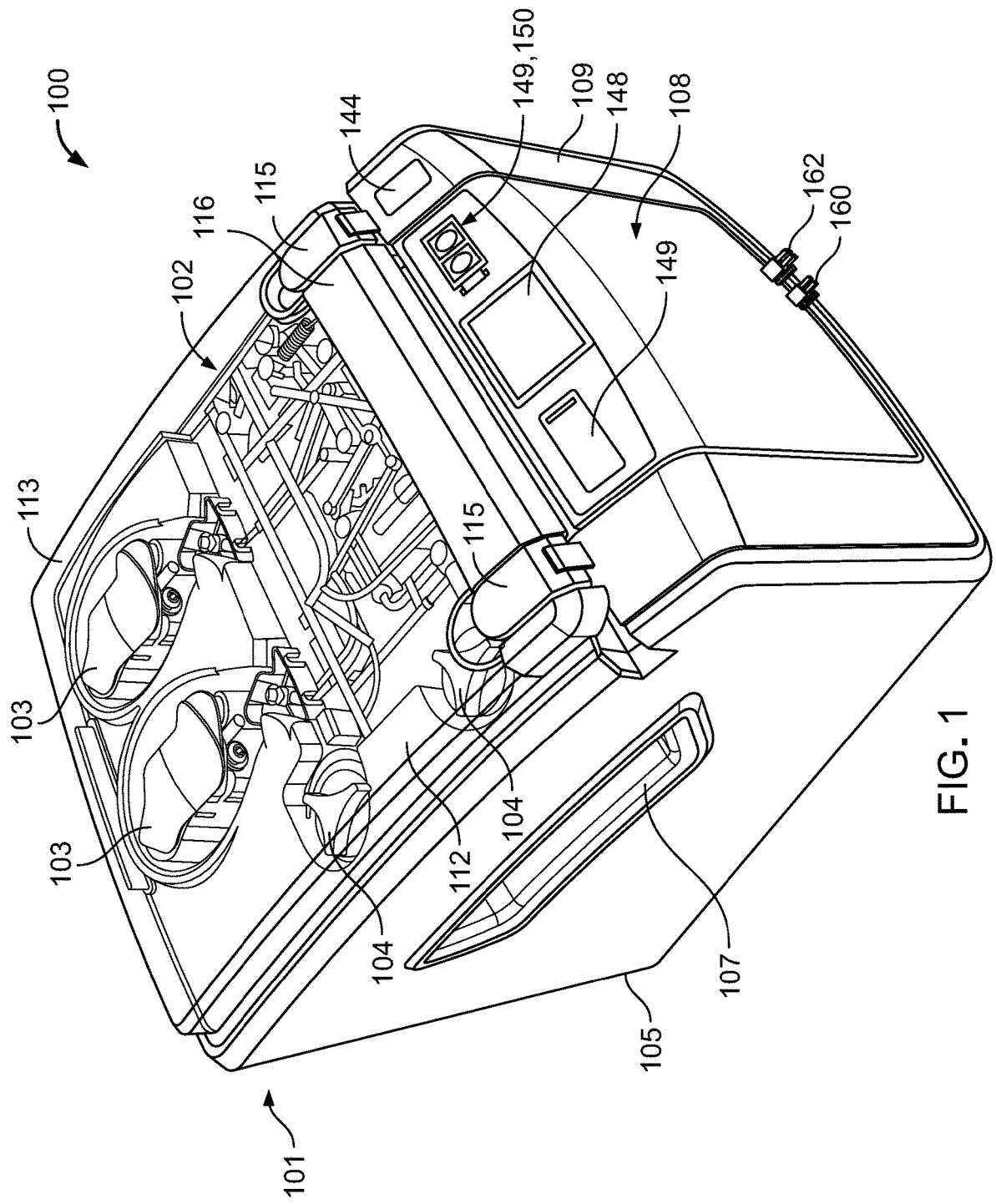
FIG. 1 is a perspective view of a fluid conditioning system that can cooperate with a dialysis system to carry out a fluid conditioning cycle that includes a dialysis treatment.
Figure 2:
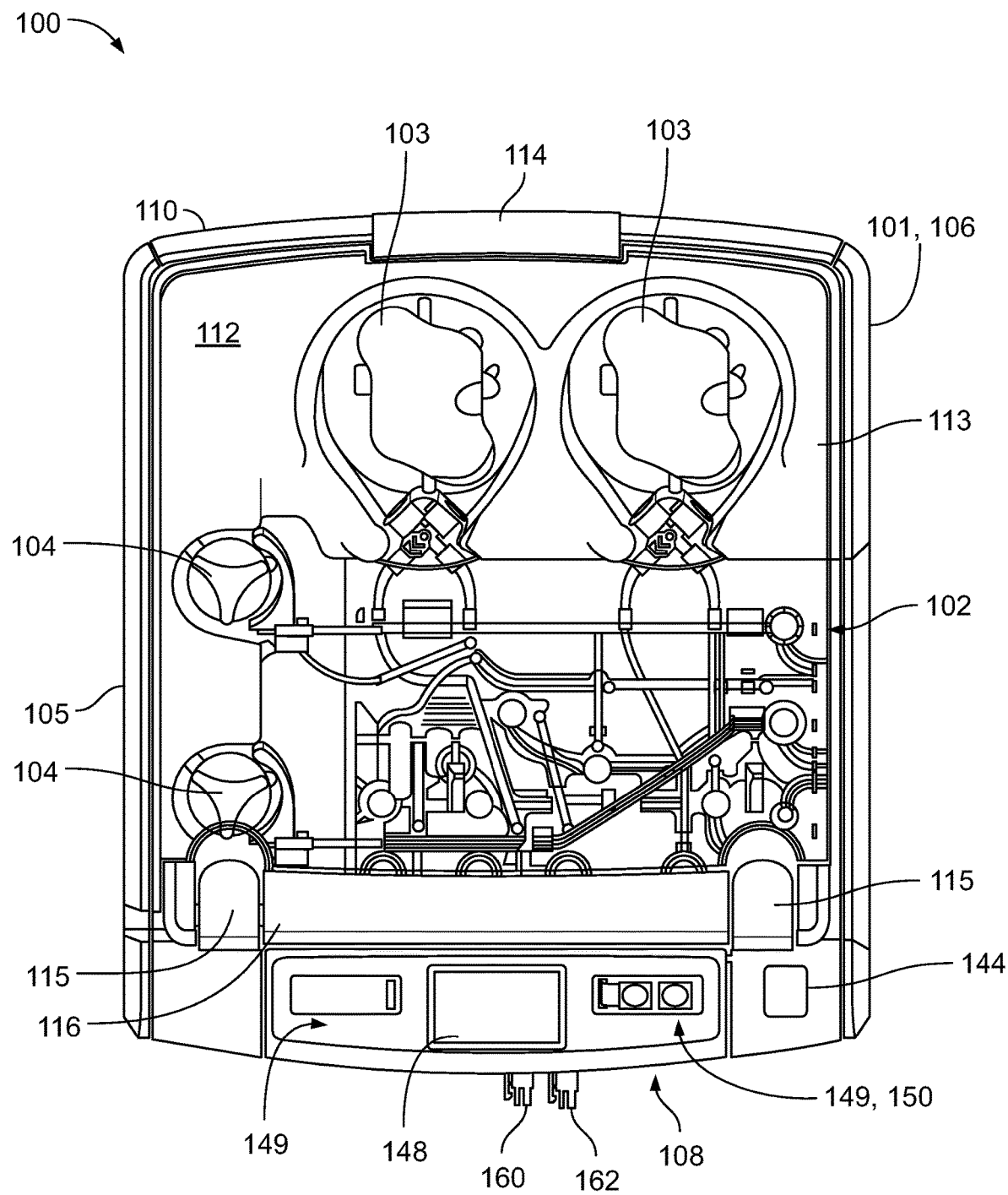
FIG. 2 is a top view of the fluid conditioning system of FIG. 1.
Figure 3:
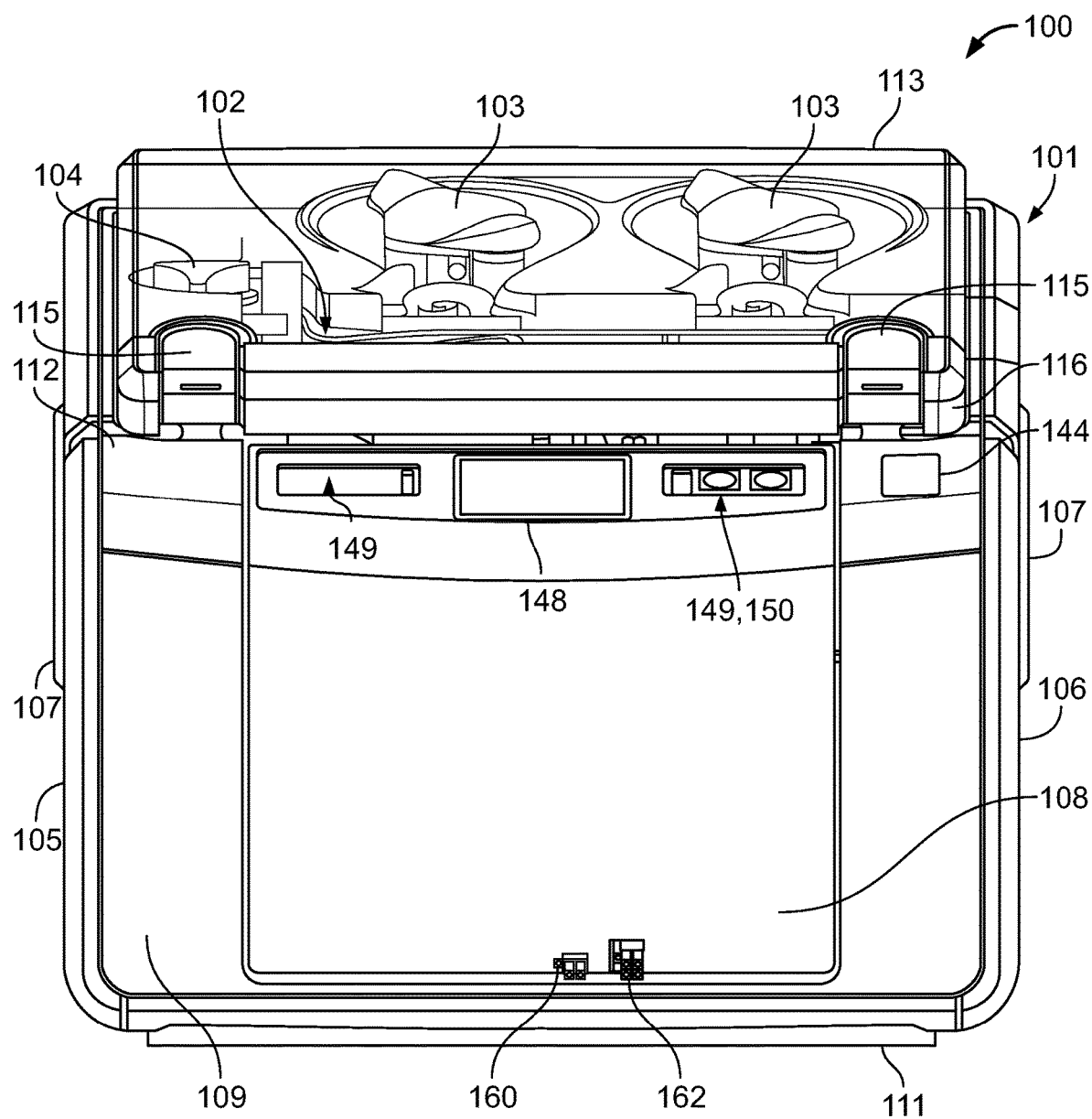
FIG. 3 is a front view of the fluid conditioning system of FIG. 1.
Figure 4:
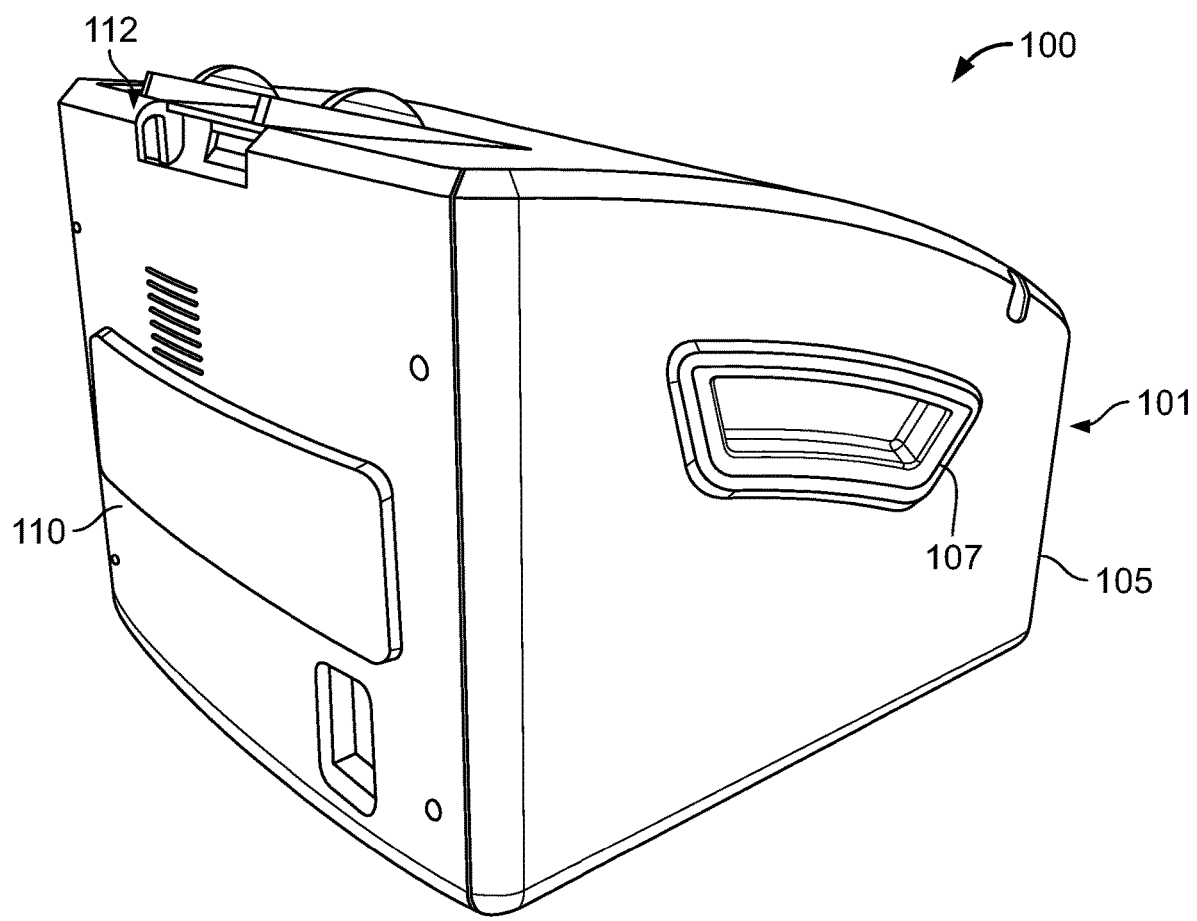
FIG. 4 is a rear view of the fluid conditioning system of FIG. 1.

FIGS. 1-4 illustrate a fluid conditioning system 100 that can be operated to prepare conditioned dialysate for use in a dialysis system. For example, the fluid conditioning system 100 can be fluidly communicated with the dialysis system to deliver "fresh" (e.g., cleaned, conditioned) dialysate to the dialysis system, collect "spent" (e.g., contaminated, unconditioned) dialysate from the dialysis system, and regenerate (e.g., cleanse) and condition the spent dialysate in a continuous fluid flow loop to recycle the spent dialysate. Example dialysis systems with which the fluid conditioning system 100 can be fluidly communicated include hemodialysis (HD) systems, peritoneal dialysis (PD) systems, hemofiltration (HF), hemodiafiltration (HDF) and other related systems.

The fluid conditioning system 100 includes a housing 101 that contains or supports components of the fluid conditioning system 100, a fluid cassette 102 that includes multiple fluid lines defining various fluid pathways, two relatively high capacity pumps 103 that can circulate fluid within the fluid lines of the fluid cassette 102, and two relatively low capacity pumps 104 that can deliver (e.g., infuse) conditioning agents into the fluid circulating within the fluid lines of the fluid cassette 102. The fluid conditioning system 100 has a compact footprint that facilitates lifting and transport of the fluid conditioning system 100. For example, the fluid conditioning system 100 typically has a length of about 30 cm to about 50 cm, a width of about 30 cm to about 50 cm, a height of about 30 cm to about 50 cm, and a weight of about 15 kg to about 20 kg.

The housing 101 includes left and right side panels 105, 106, handles 107 positioned along the side panels 105, 106 for carrying the fluid conditioning system 100, a door assembly 108 that can be opened and closed to insert a heater bag, a front panel 109 to which the door assembly 108 is secured, rear and bottom panels 110, 111 that further enclose the interior components, an upper panel 112 that supports the fluid cassette 102 and the pumps 103, 104, and a cover 113 that protects the fluid cassette 102 and the pumps 103, 104. Example materials from which the exterior panels of the housing 101 may be made include plastics, such as acrylonitrile butadiene styrene (ABS) and polycarbonate blends, among others.

The cover 113 is typically made of ABS or polycarbonate and is transparent or translucent to allow visualization of the fluid cassette 102 and the pumps 103, 104. The cover 113 can be pivoted at a rear hinge 114 disposed along the upper panel 112 to open or close the cover 113. The upper panel 112 carries two latches 115 that can be closed upon a front edge 116 of the cover 113 to secure the cover 113 in a closed position. The latches 115 can also be pulled up and apart from the cover 113 to release the cover 113 from the closed position for accessing the fluid cassette 102 and the pumps 103, 104.

Figure 5:
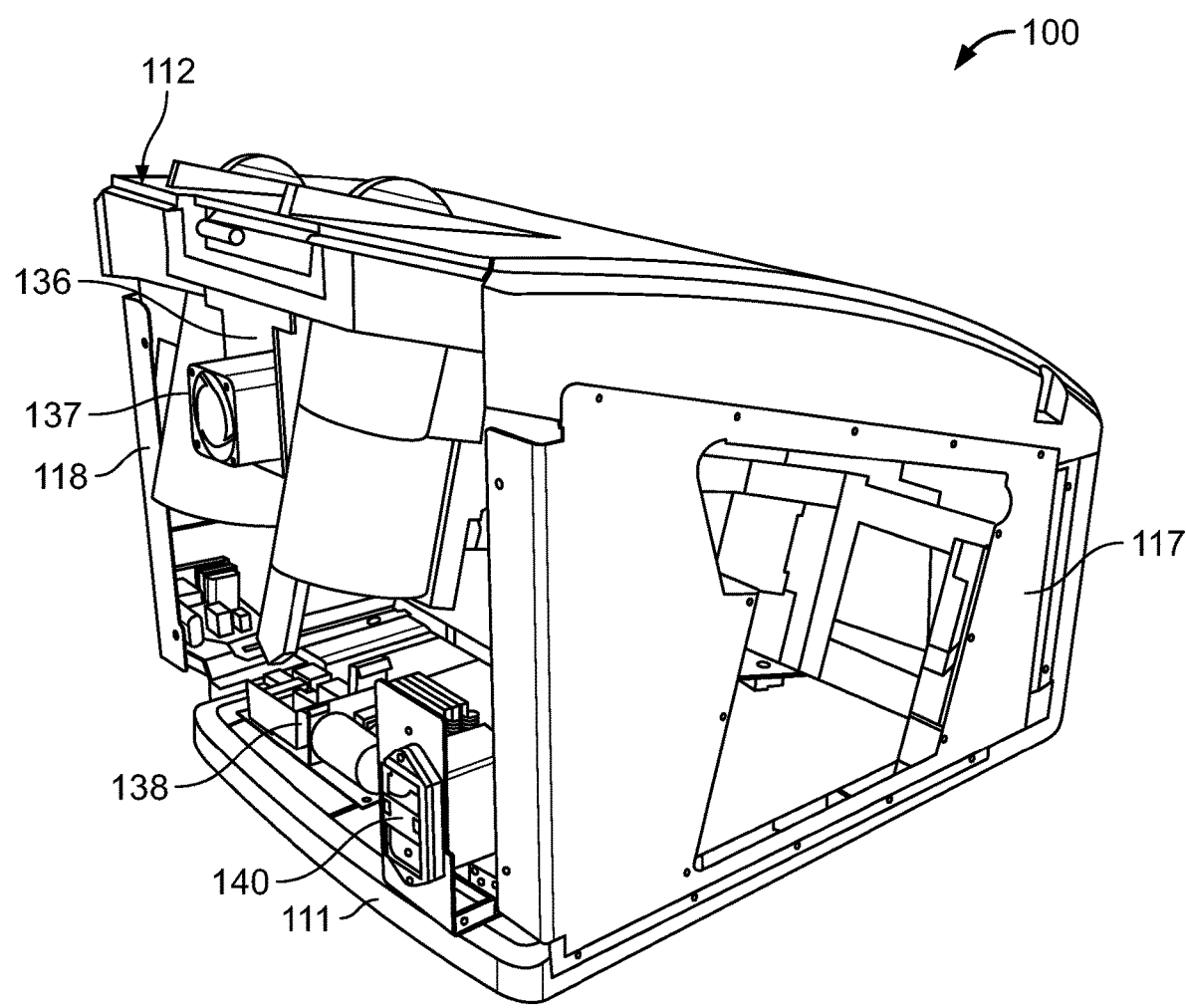
FIG. 5 is a rear view of the fluid conditioning system of FIG. 1, with certain exterior components omitted to expose certain interior components.

Referring to FIG. 5, the fluid conditioning system 100 also includes left and right side interior support frames 117, 118 to which the left side, right side, front, rear, bottom, and upper panels 105, 106, 109, 110, 111, 112 are attached. The interior support frames 117, 118 are typically formed from sheet metal.

Each pump 103, 104 is a peristaltic pump that includes multiple rollers positioned about the circumference of a rotatable frame (e.g., a motor) that carries a fluid line extending from the fluid cassette 102. As the rotatable frame is rotated, the rolling members apply pressure to the fluid line, thereby forcing fluid to flow through the fluid line.

Figure 6:
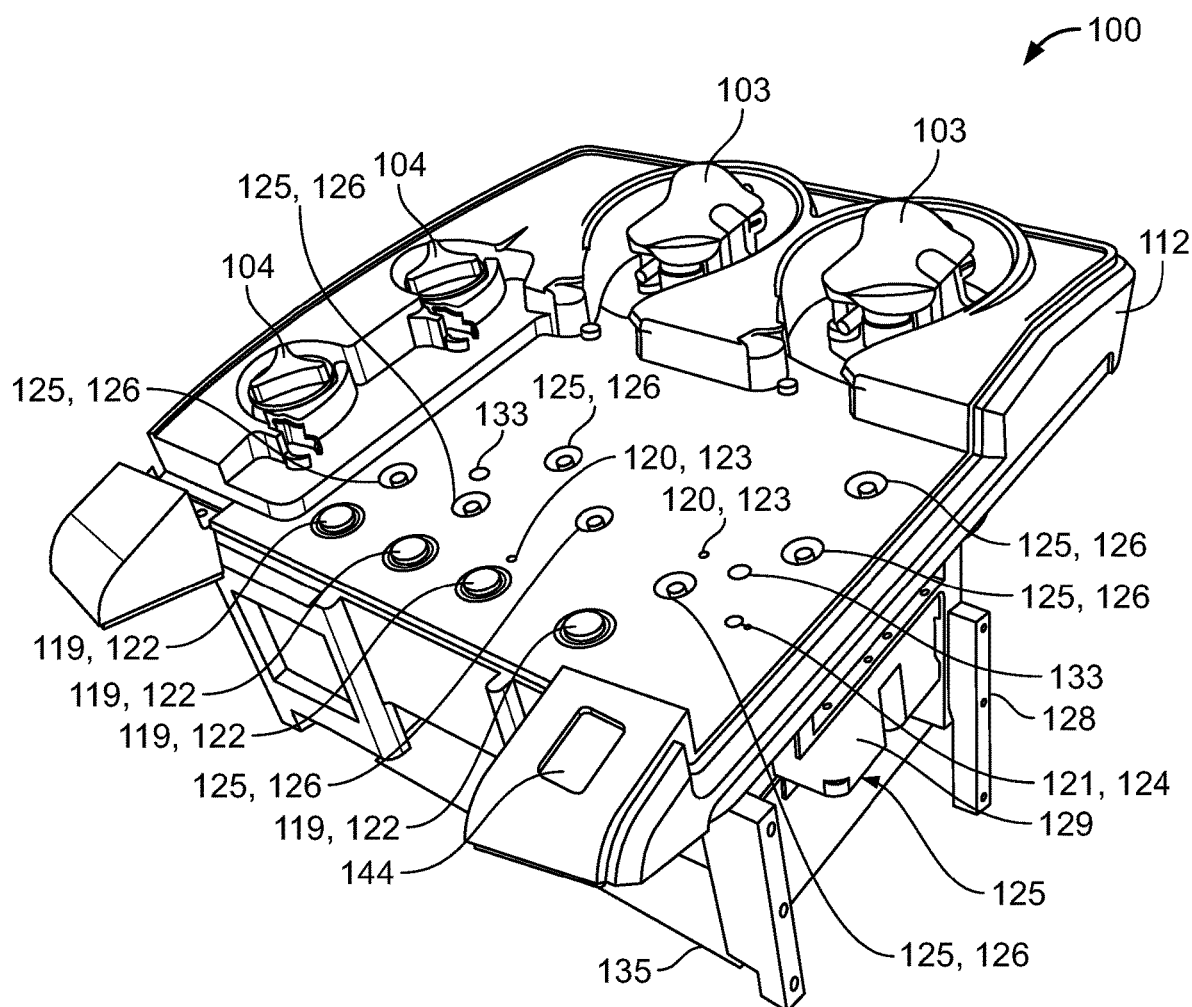
FIG. 6 is a perspective view of the fluid conditioning system of FIG. 1, with certain exterior components omitted to expose certain interior components.
Figure 7:
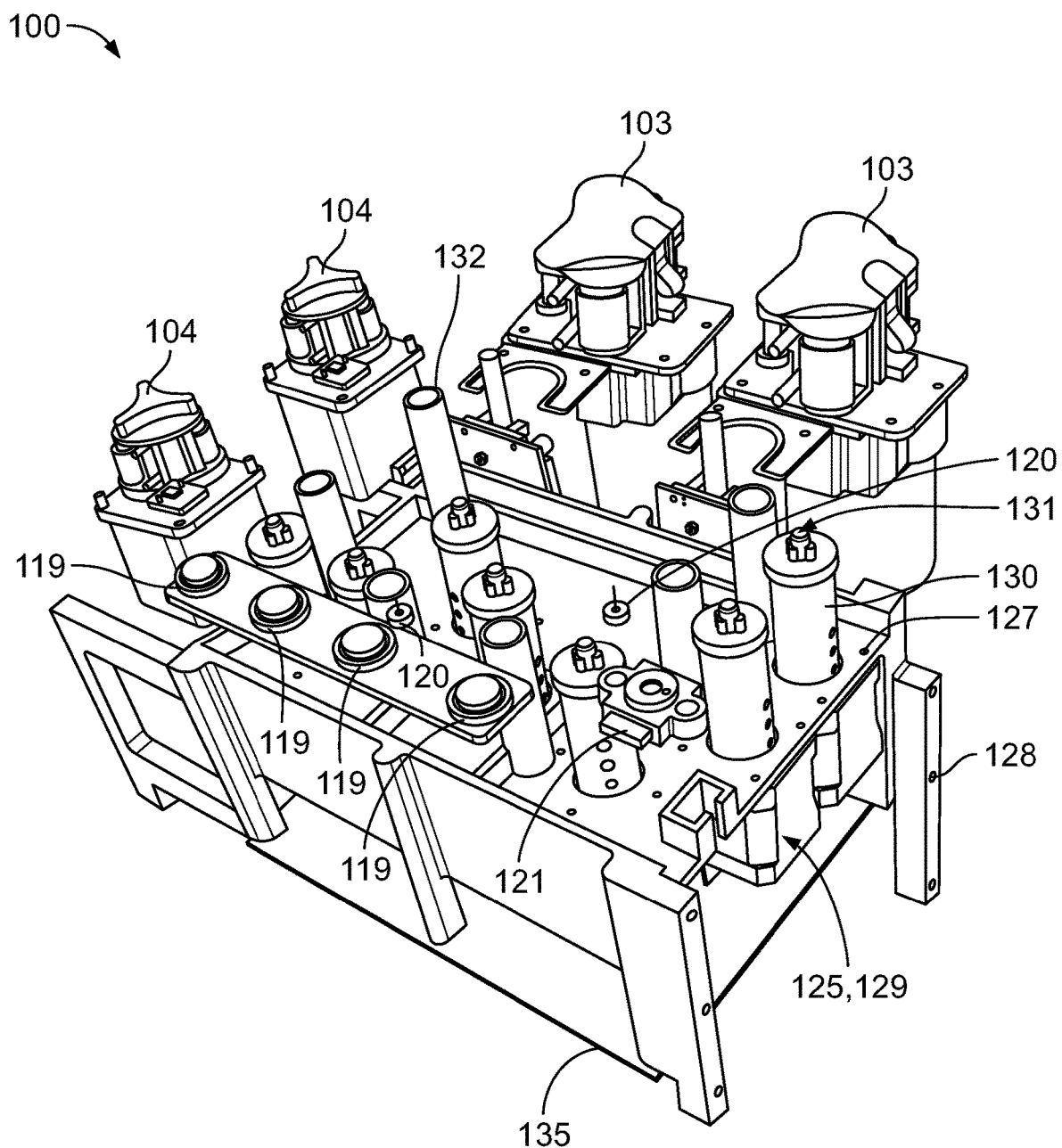
FIG. 7 is a perspective view of the fluid conditioning system of FIG. 1, with certain exterior components omitted to expose certain interior components.
Figure 8:
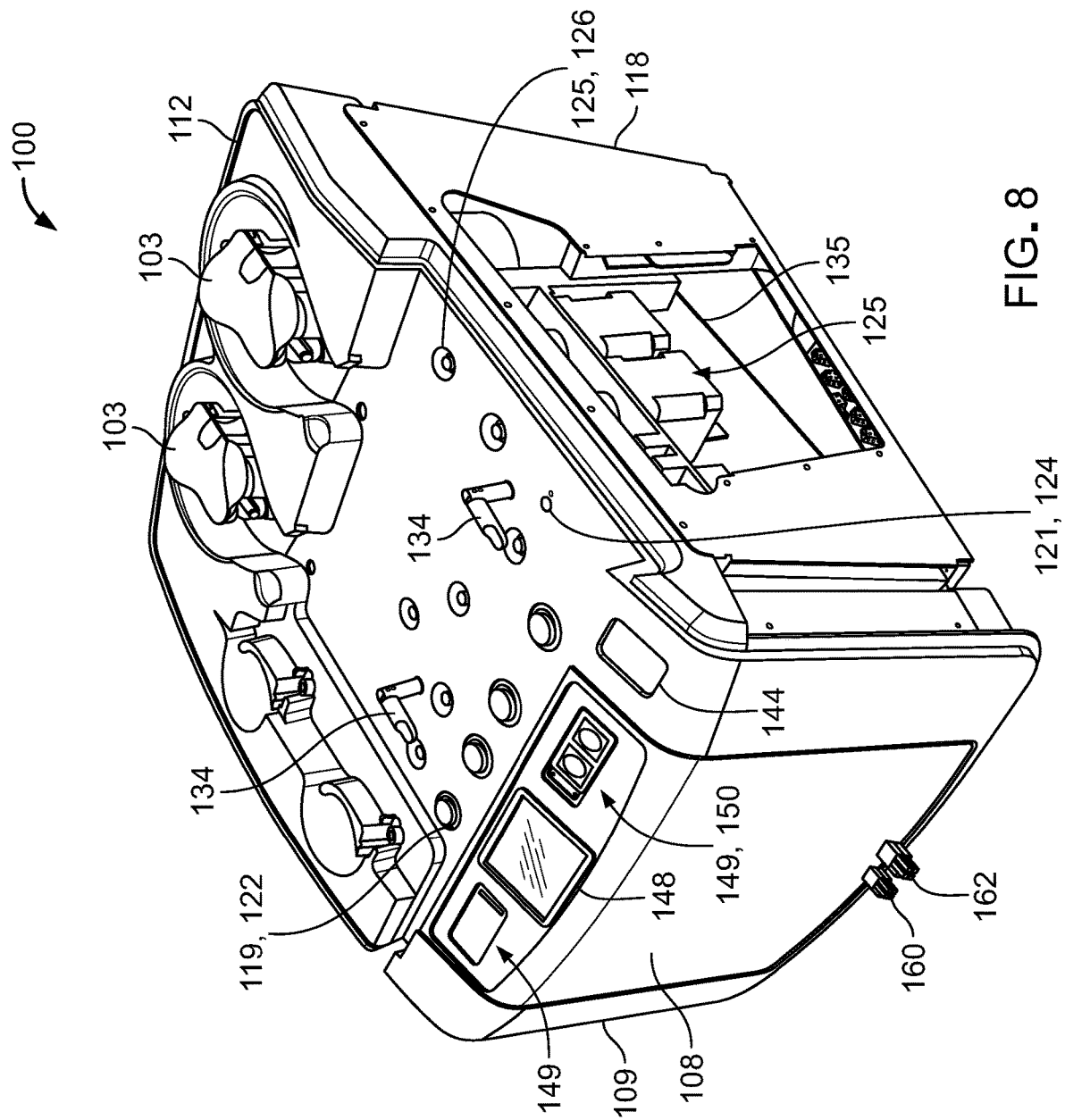
FIG. 8 is a perspective view of the fluid conditioning system of FIG. 1, with certain exterior components omitted to expose certain interior components.

FIGS. 6-8 illustrate certain interior components of the fluid conditioning system 100. For example, the fluid conditioning system 100 further includes multiple pressure transducers 119, two temperature sensors 120, and an ammonia detector 121 that are respectively positioned within holes 122, 123, 124 in the upper panel 112 for engagement with the fluid cassette 102. The pressure transducers 119 are embodied as thin, flexible membranes that contact corresponding thin, flexible membranes 164 within the fluid cassette 102 (refer to FIG. 15) for detecting fluid pressures within certain fluid pathways of the fluid cassette 102. The temperature sensors 120 are infrared (IR) sensors that detect temperatures of the dialysate flowing through certain points of the fluid pathways of the fluid cassette 102. The ammonia detector 121 is a red-green-blue (RGB) color sensor that can detect color changes on a paper strip within the fluid cassette 102 for determining a concentration of ammonium (e.g., which generates ammonia) within the dialysate flowing through a certain fluid pathway of the fluid cassette 102. The fluid conditioning system 100 also includes circuitry that acquires and conditions signals generated by conductivity sensors that are provided on the fluid cassette 102, which will be discussed in more detail below.

The fluid conditioning system 100 also includes multiple actuators 125 that are aligned with holes 126 in the upper panel 112 for respectively and selectively moving multiple valves of the fluid cassette 102. Each actuator 125 is mounted to a platform 127 of an internal frame 128 of the fluid conditioning system 100 and includes a motor 129 and a drive unit 130 that can be moved (e.g., rotated or otherwise manipulated) by the motor 129. The drive unit 130 is equipped with a coupling member 131 that is formed to engage a respective valve of the fluid cassette 102 such that movement of the drive unit 130 produces movement of the valve. The internal frame 128 also includes columnar support members 132 that support and locate the upper panel 112 of the housing 101. The upper panel 112 further defines holes 133 that are positioned and sized to receive locating pins 134 for appropriately positioning the fluid cassette 102 with respect to the upper panel 112. With the fluid cassette 102 in place, the locating pins 134 can be snapped down toward the upper panel 112 to lock the position of the fluid cassette 102. The fluid conditioning system 100 also includes a circuit board 135 equipped with electronics for operating the various electromechanical components of the fluid conditioning system 100. For example, the electronics execute codes for carrying out the various stages of a fluid conditioning cycle (as discussed below with reference to FIGS. 18-20), operating the pumps 103, 104, turning valves for the fluid cassette 102, processing sensor signals, operating the actuators 125, operating a heater assembly 151, and running control loops (e.g., control loops for regulating dialysate temperature, regulating pump speeds to achieve desired flow rates, regulating pump speeds to achieve desired dialysate chemical compositions, and ensuring device safety).

Referring again to FIG. 5, the fluid conditioning system 100 further includes a support bracket 136 and a fan 137 carried therein for cooling the circuit board 135 and other internal components of the fluid conditioning system 100. The fluid conditioning system 100 also includes a power supply 138, as well as a support bracket 139 that carries an A/C-in port 140.

Figure 10:
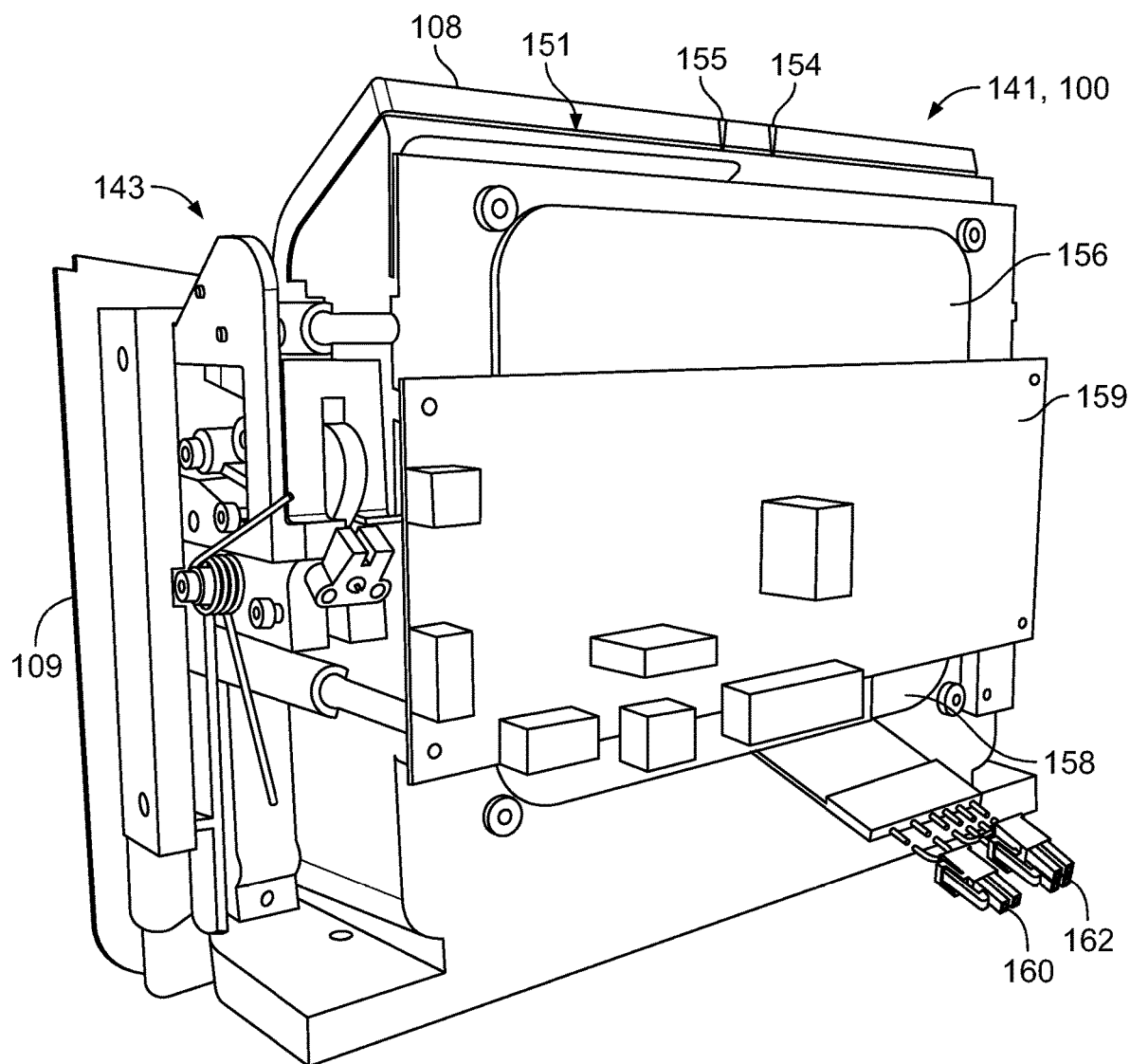
FIG. 10 is a rear perspective view of the front assembly of FIG. 9.
Figure 11:
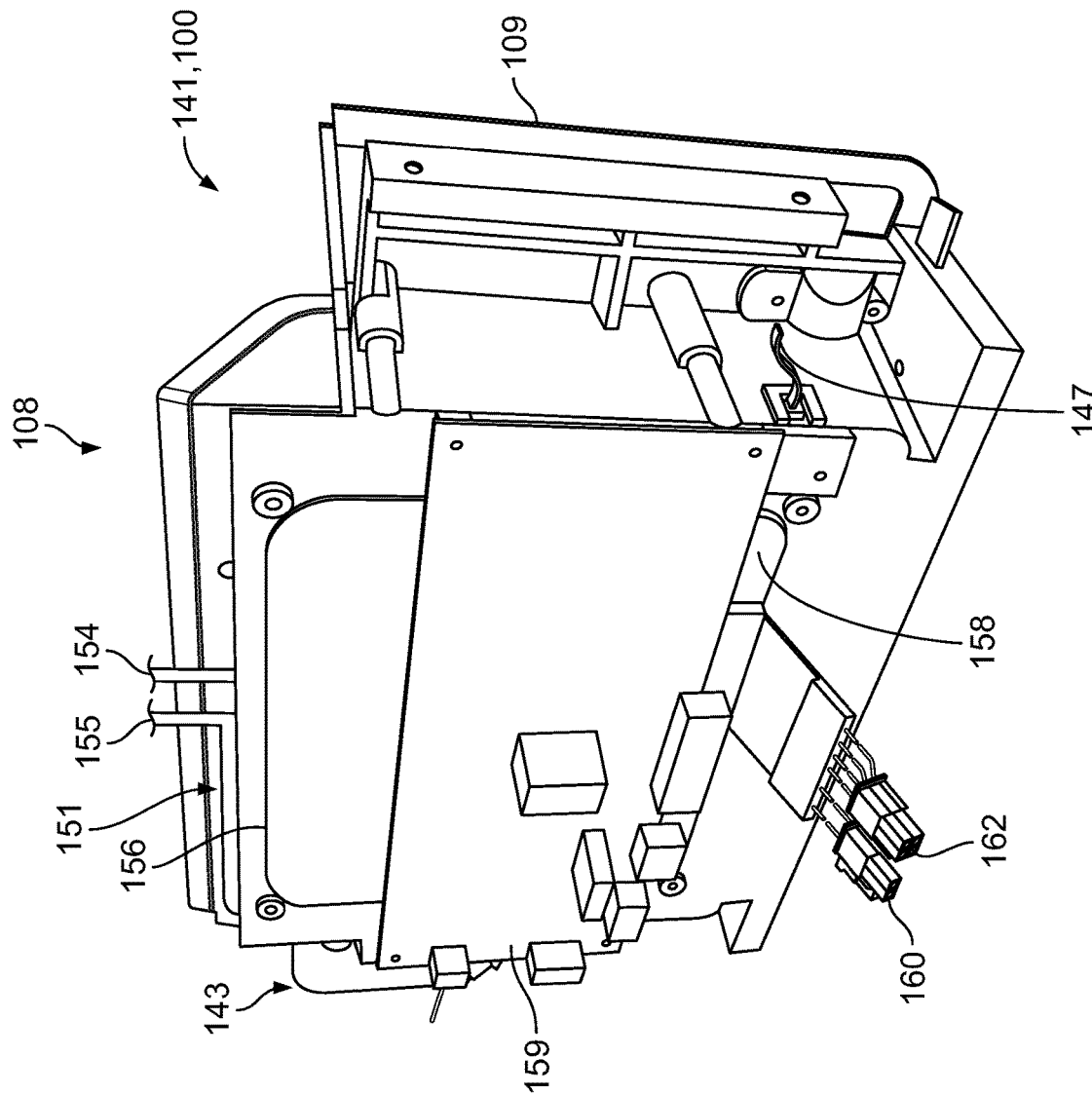
FIG. 11 is a rear perspective view of the front assembly of FIG. 9.
Figure 12:
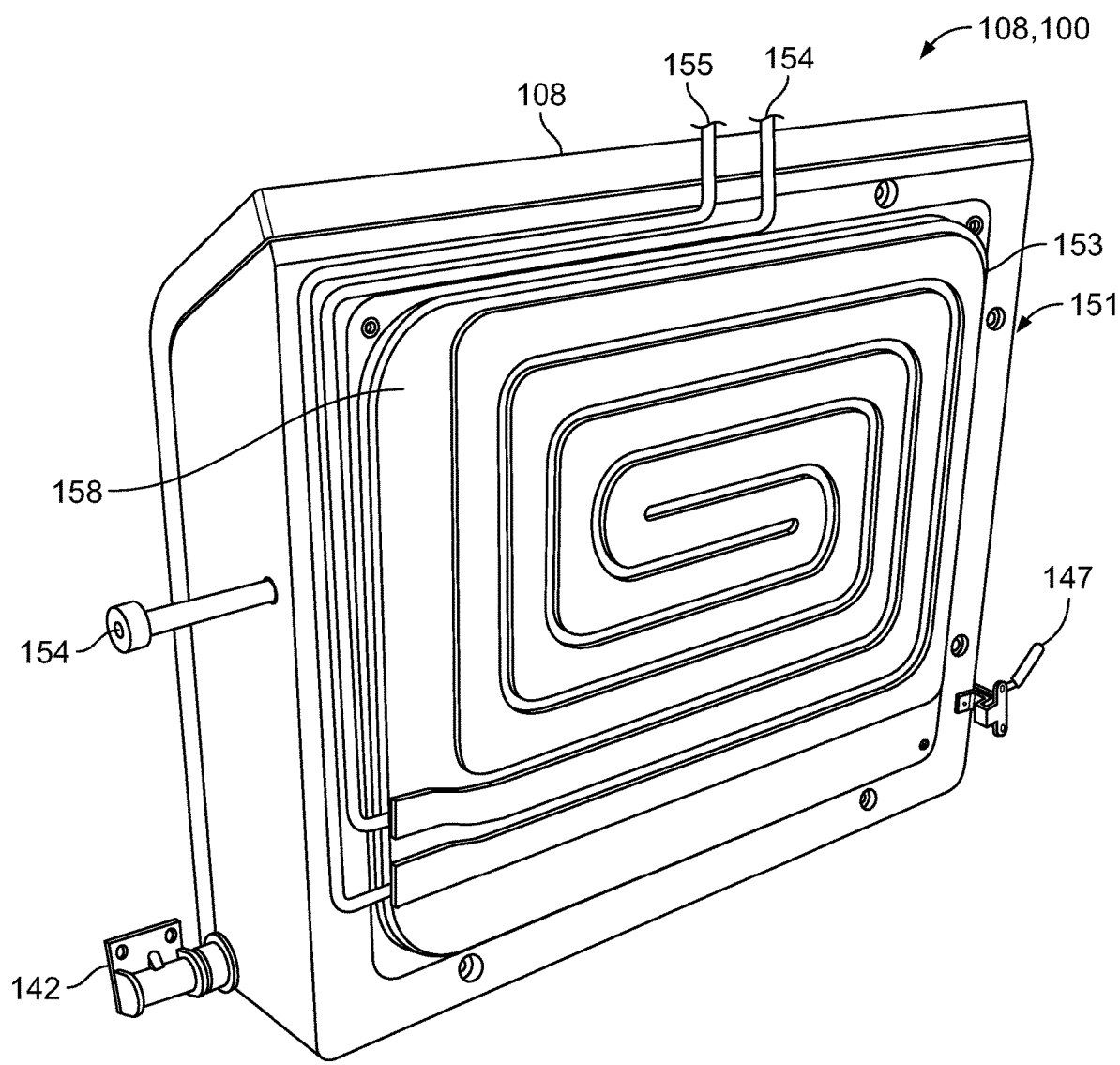
FIG. 12 is a rear perspective view of a heater bag of a door assembly of the front assembly of FIG. 9.

FIGS. 9-13 illustrate various views of a front assembly 141 of the fluid conditioning system 100. The front assembly 141 includes the door assembly 108 and the front panel 109 of the housing 101. The door assembly 108 is pivotable at hinges 142 with respect to the front panel 109 to allow loading of the heater bag 153 into the fluid conditioning system 100. The hinges 142 are friction hinges located along opposite sides of the door assembly 108, as shown in FIG. 12.

Figure 13:
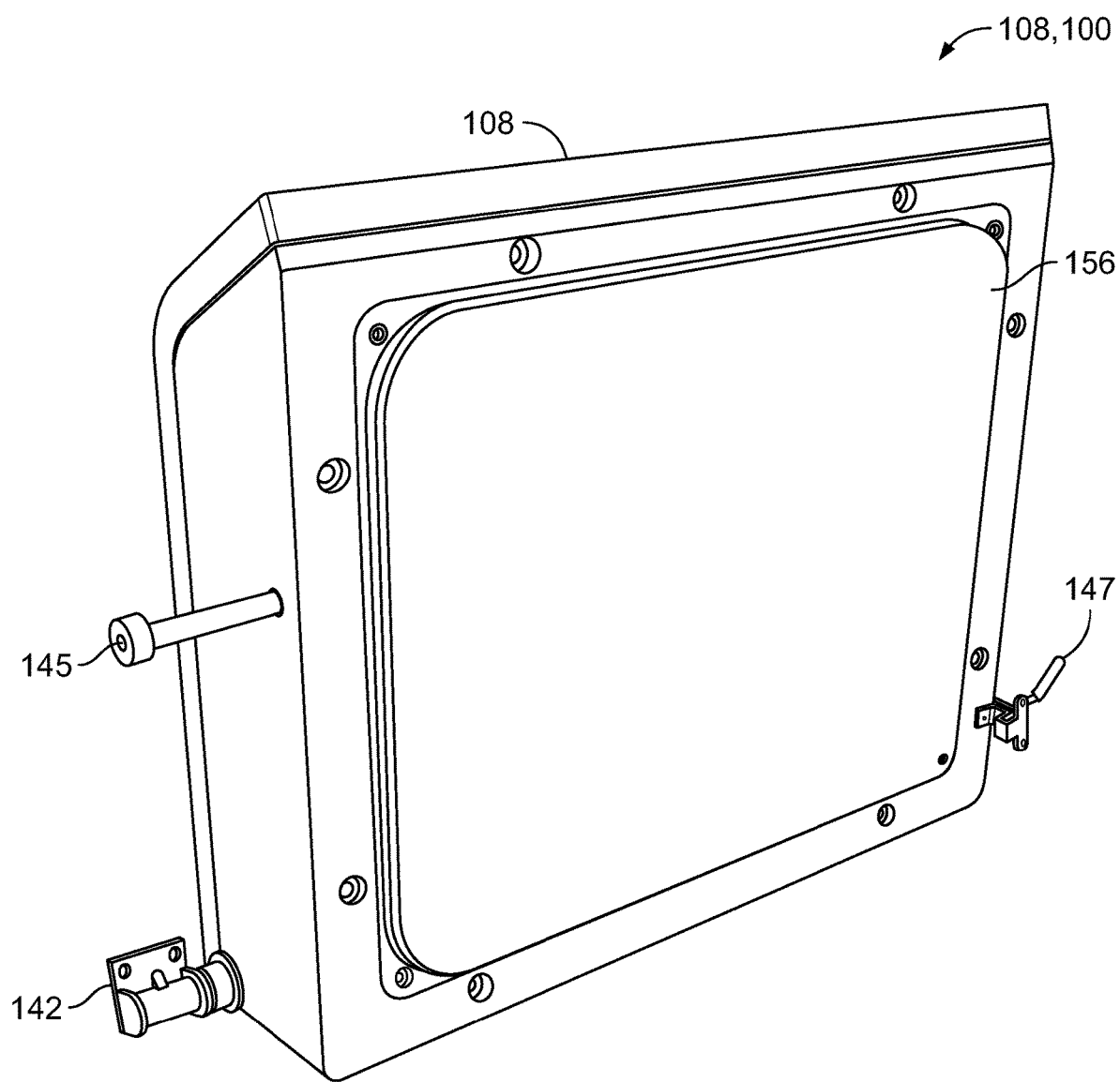
FIG. 13 is a rear perspective view of a heater plate of a door assembly of the front assembly of FIG. 9.

The front panel 109 carries a latch assembly 143 that cooperates with a button 144 carried by the upper panel 112 (shown in FIGS. 1-4) to releasably secure the door assembly 108 to the front panel 109 in a closed position. For example, depression of the button 144 adjusts the latch assembly 143 so that the door assembly 108 can be unlocked from a closed position and pivoted to an open position. The door assembly 108 can alternatively be pivoted inward from an open configuration until oppositely positioned screws 145 (e.g., shoulder screws, shown in FIG. 12) engage the latch assembly 131 to lock the door assembly 108 in the closed position. The latch assembly 131 has a contact switch for determining whether the door assembly 108 is open or closed. Referring particularly to FIGS. 11 and 13, the door assembly 108 includes an optical switch 147 that indicates whether or not the heater bag is inserted. In some embodiments, the fluid conditioning system 100 may be inoperable when the door assembly 108 is open.

Figure 9:
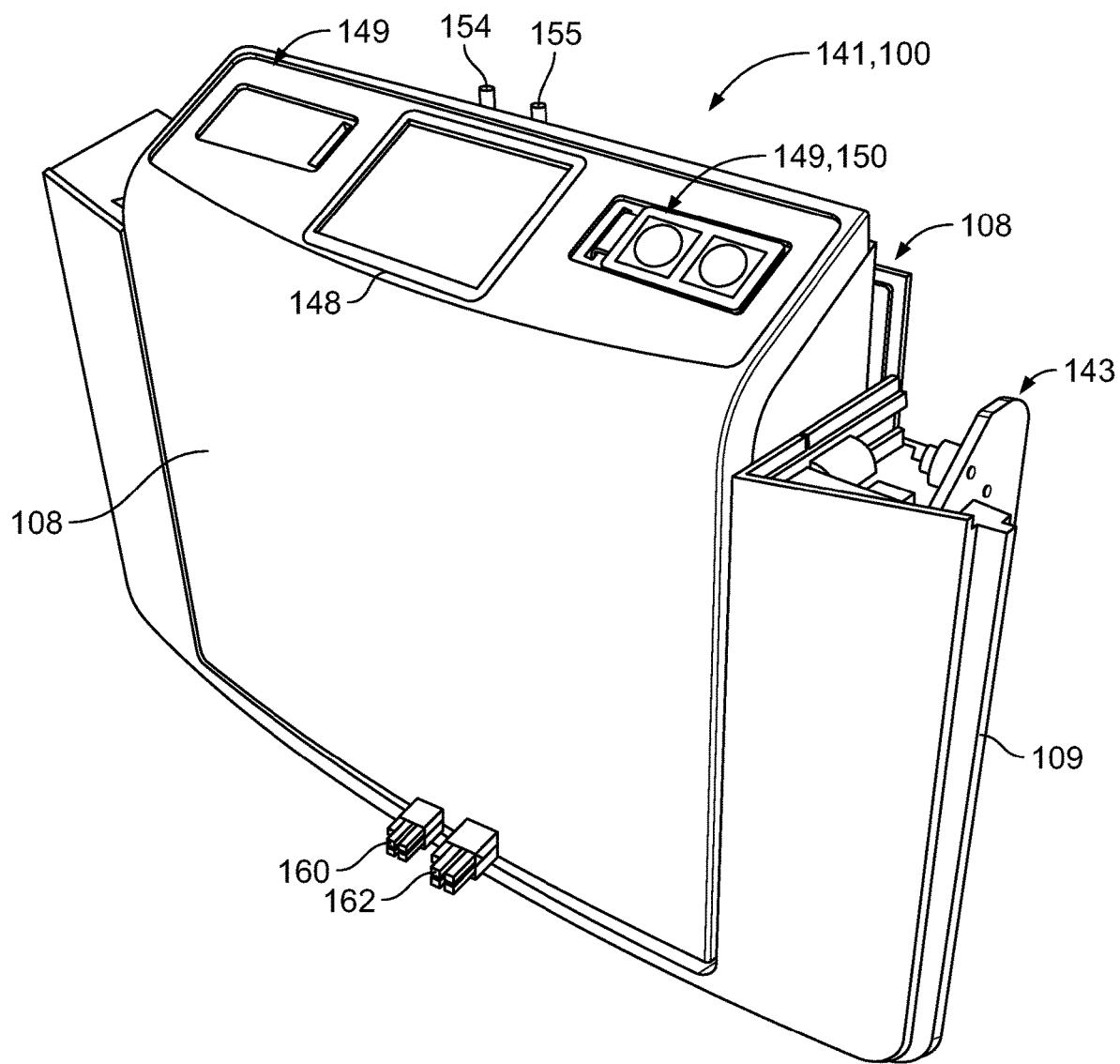
FIG. 9 is a perspective view of a front assembly of the fluid conditioning system of FIG. 1.

Referring particularly to FIG. 9, the door assembly 108 supports a display screen 148 (e.g., a touchscreen display) on which graphical user interfaces (GUIs) can be displayed and two control panels 149 that can each be equipped with selectors 150 (e.g., buttons) for providing inputs at the GUIs to operate the fluid conditioning system 100. Example parameters and processes that may be controlled by a user via the display screen 148 using the selectors 150 include starting and stopping a treatment, initiating a drain cycle, changing a flowrate, initiating a priming stage of a fluid conditioning cycle, initiating system preparation to start a fluid conditioning cycle, adjusting a temperature according to patient comfort, confirming correct placement of the fluid cassette 102, or confirming correct placement of fluid lines that interface with the pumps 103, 104.

Referring to FIGS. 10-13, the front assembly 141 includes components of a heater assembly 151 that is designed to regulate fluid temperatures of dialysate transported along the fluid pathways of the fluid cassette 102. Referring particularly to FIG. 12, the heater assembly 151 includes a heater bag 153 that is equipped with an input connection 154 and an output connection 155 that can interface with the fluid cassette 102 for allowing dialysate to circulate through the heater bag 153 to be warmed. The heater bag 153 is formed as a plastic channel that has a generally flat, collapsed shape when empty, that inflates upon filling with fluid, and that transfers heat from an exterior surface to dialysate flowing through the heater bag 153.

Figure 14:
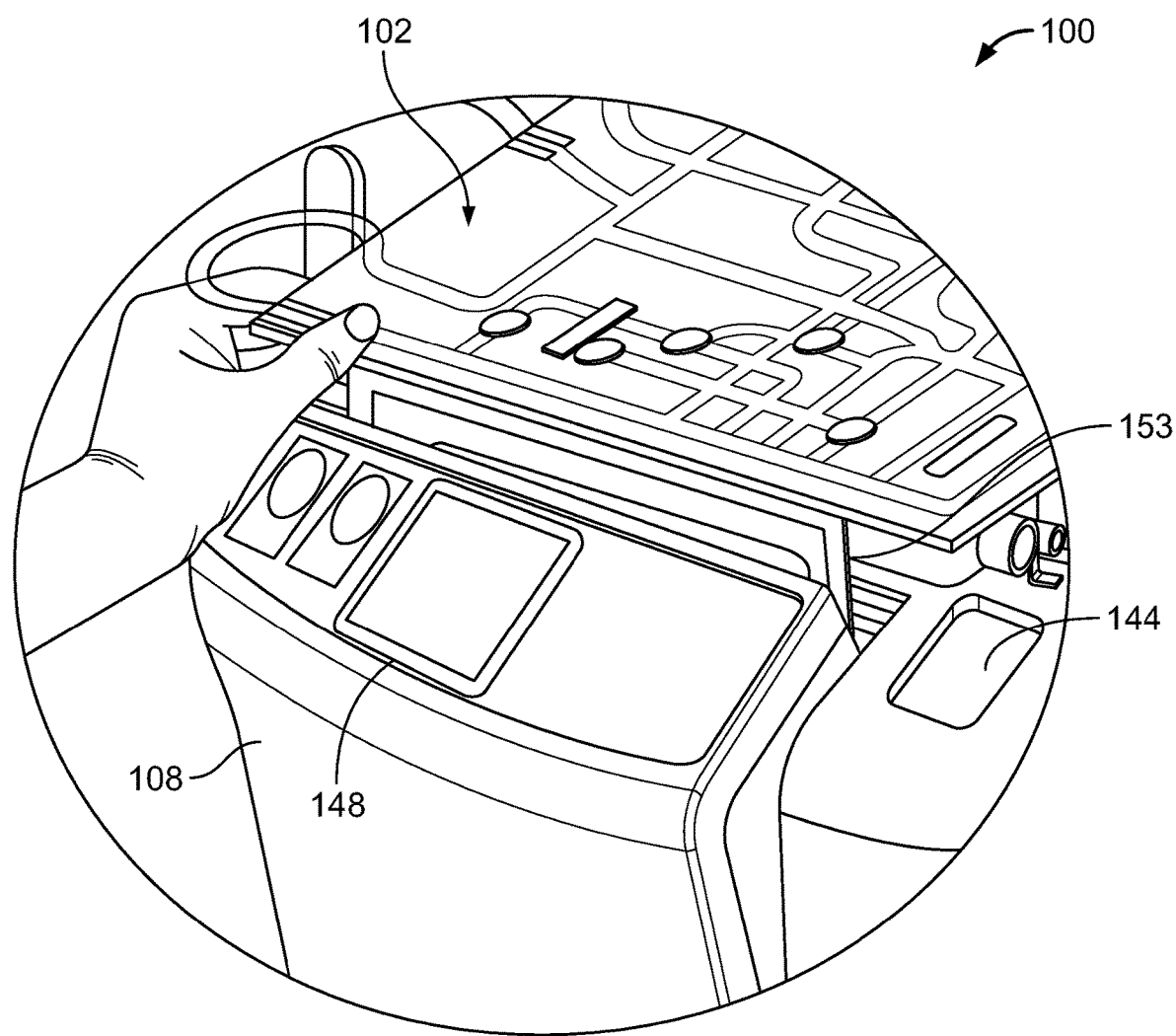
FIG. 14 is a perspective view illustrating installation of the heater bag of FIG. 12 and a fluid cassette of the fluid conditioning system of FIG. 1.

Referring particularly to FIG. 13, the heater assembly 151 further includes two plates 156 (e.g., aluminum plates) that position and support the heater bag 153 and that are heated for transferring heat to fluid within the heater bag 153. Referring particularly to FIG. 14, the heater bag 153 can be slid between the two heater plates 156 (not visible in FIG. 14) within the door assembly 108 when the door assembly 108 is in the open configuration. Referring particularly to FIGS. 10-12, the heater assembly 151 further includes one or more heating elements (for example, resistive type heating elements that are not shown) by which fluid in the heater bag 153 can be warmed and two insulation pads 158 disposed on opposite sides of the heater bag 153. The one or more heating elements are carried by or otherwise attached to one or both of the plates. The heater assembly 151 also includes a circuit board 159 that provides electronics for operating the heater assembly 151, a feed line 160 for each heating pad 156 that provides power, and thermocouple connections 162 for determining a temperature of the respective heating plates 156.

Figure 15:
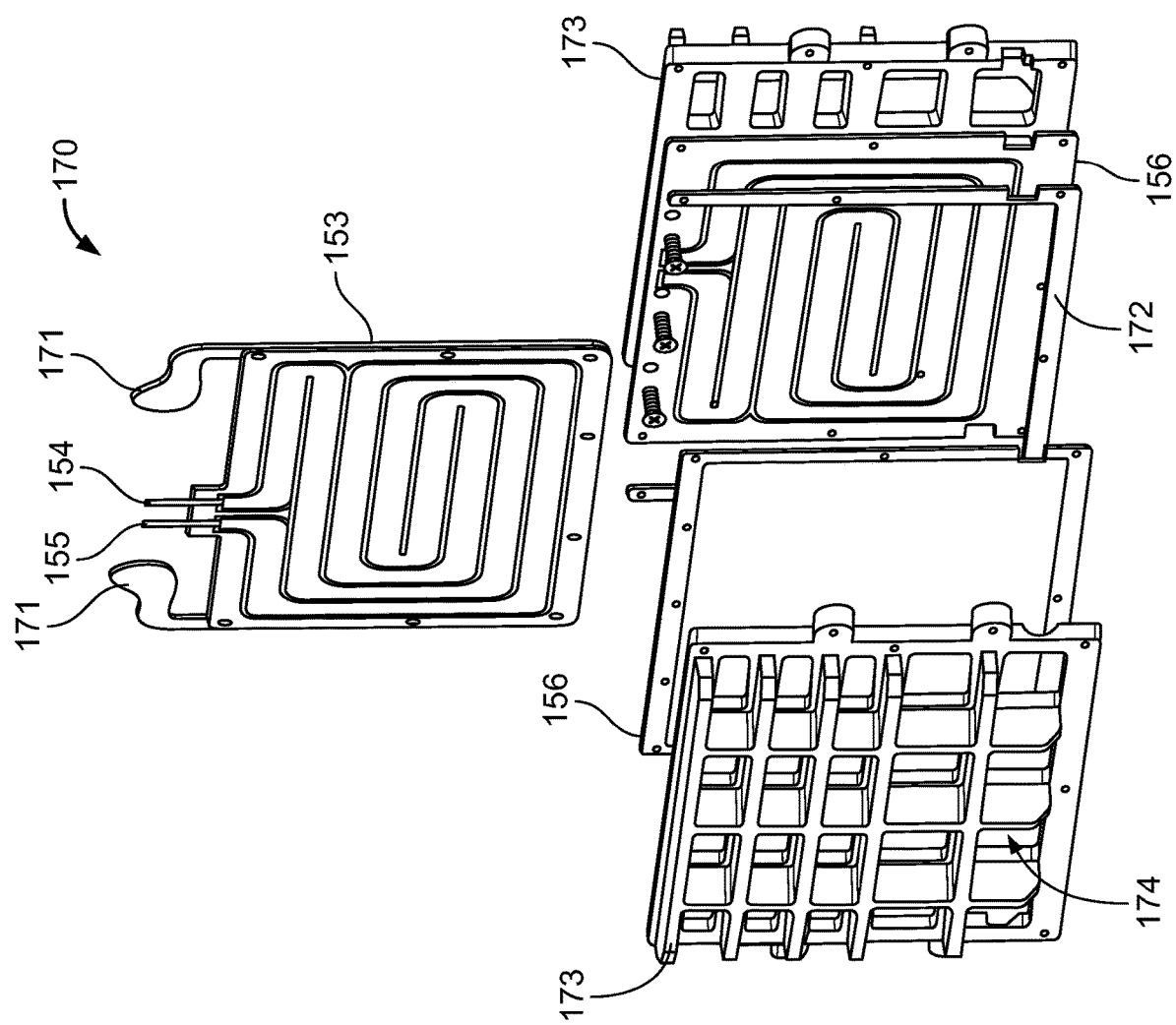
FIG. 15 is a perspective view of the fluid cassette of FIG. 14, along with the heater bag of FIG. 12.
Figure 16:
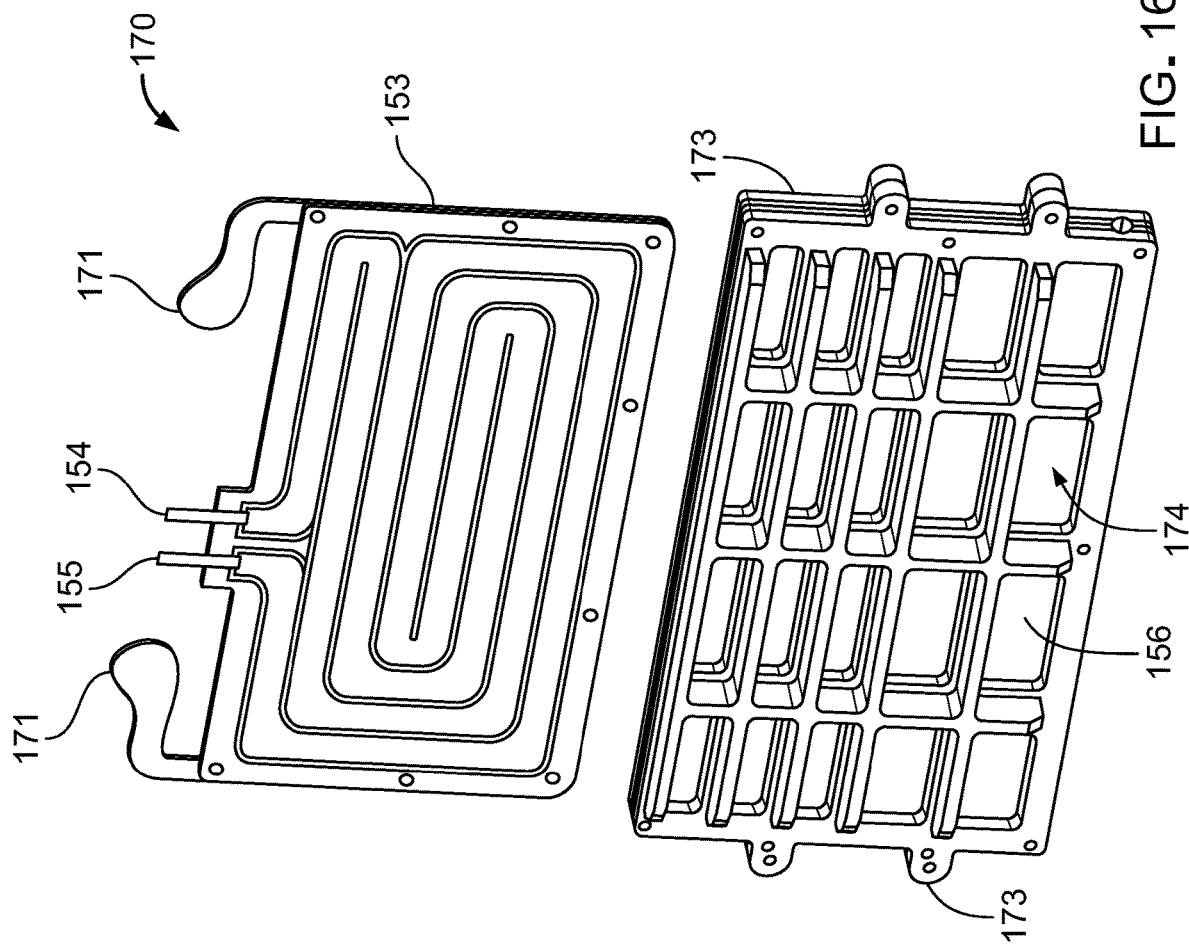
FIG. 16 is a full exploded perspective view of an embodiment of a heater assembly that may be included within the fluid conditioning system of FIG. 1.

FIGS. 15 and 16 illustrate another embodiment of a heater assembly 170 that may be included in the fluid conditioning system 100 instead of the heater assembly 151. The heater assembly 170 is similar in construction and function to the heater assembly 151 and accordingly includes the heater bag 153 sandwiched between the two heater plates 156. The heater assembly 170 further includes two handles 171 attached to the heater bag 153 for easy placement of the heater bag 153, a u-shaped heater frame 172 that supports the heater bag 153, and two support members 173 of a generally matrix construction that support the heater plates 156. The support members 173 further serve to insulate the heater bag 153 and the heater plates 156 from surrounding components via air gaps 174 defined by the matrix construction that are disposed between the heater plates 156 and such components.

Figure 17:
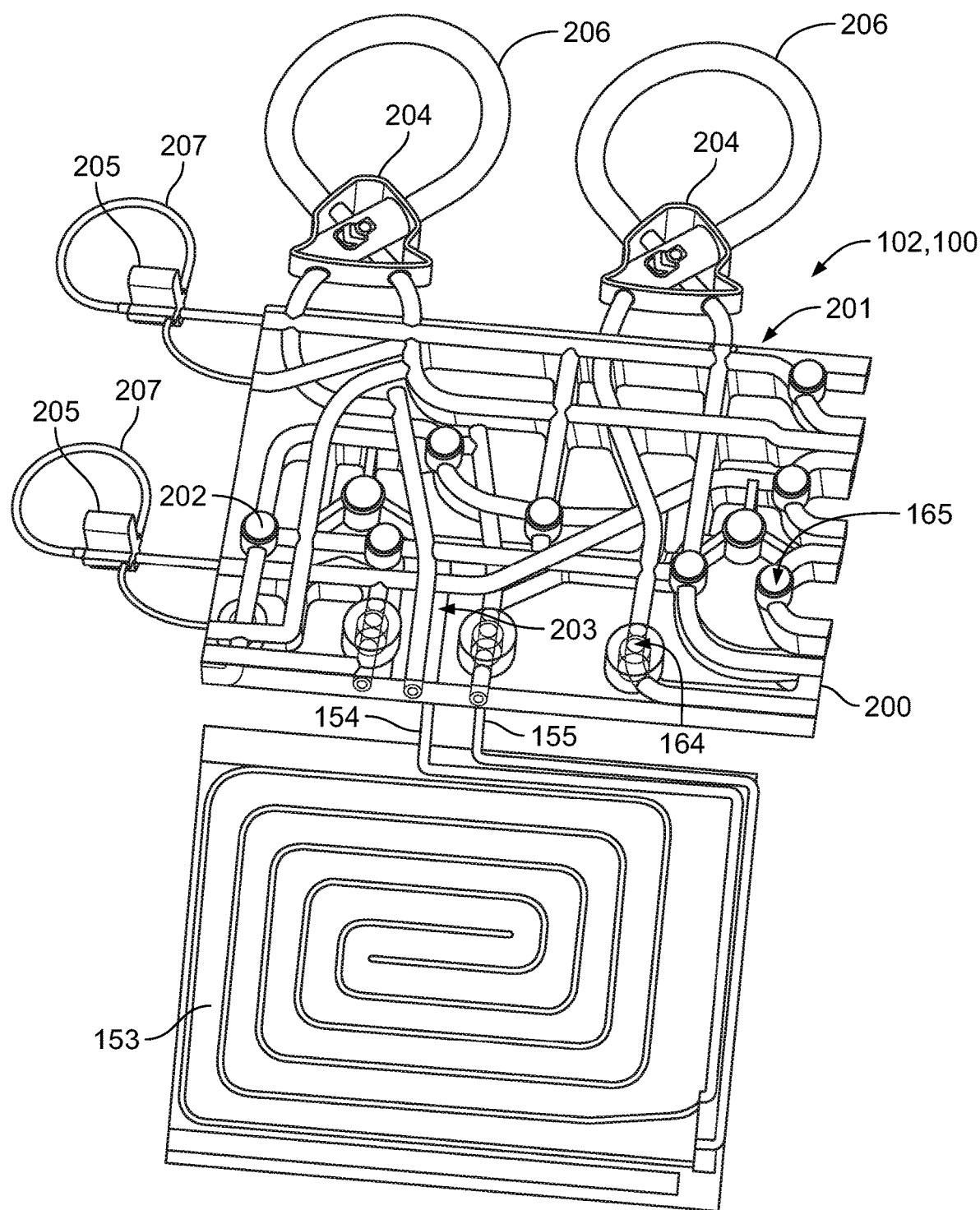
FIG. 17 is a partially exploded perspective view of the heater assembly of FIG. 16.

Referring to FIG. 17, the fluid cassette 102 is a single-use, disposable cartridge that includes a housing 200, multiple fluid lines 201 arranged within the housing 200, multiple valves 202 positioned along the fluid lines 201, two conductivity sensors 203 positioned along the fluid lines 201, an ammonia sensor 165 positioned along the fluid lines 201 for cooperation with the ammonia detector 121, two fluid line connectors (e.g., pump segment clips) 204, and two fluid line connectors (e.g., pump segment clips) 205. The fluid lines 201 cooperate with the heater bag 153 and a dialysis system to form a fluid circuit 350 for carrying out a fluid conditioning cycle. For example, the fluid lines 201 include ports to which the input and output connections 154, 155 of the heater bag 153 can be connected for providing fluid communication between the fluid lines 201 and the heater bag 153. The fluid line connectors 204 locate fluid line segments 206 about the high-capacity pumps 103, and the fluid line connectors 205 locate fluid line segments 207 about the low-capacity pumps 104. The fluid cassette 102 also includes additional fluid lines that extend from the fluid cassette 102 to various fluid containers, as illustrated in FIG. 19.

The valves 202 are three-way valves by which two alternative fluid pathways can be selected by a control system of the fluid conditioning system 100. Lower portions of the valves 202 are formed to engage with the coupling members 131 of the actuators 125 for movement of the valves 202. Example types of valves 202 that may be included in the fluid cassette 102 include rotary valves, push-pull valves, sliding valves, and shuttle valves.

Figure 18:
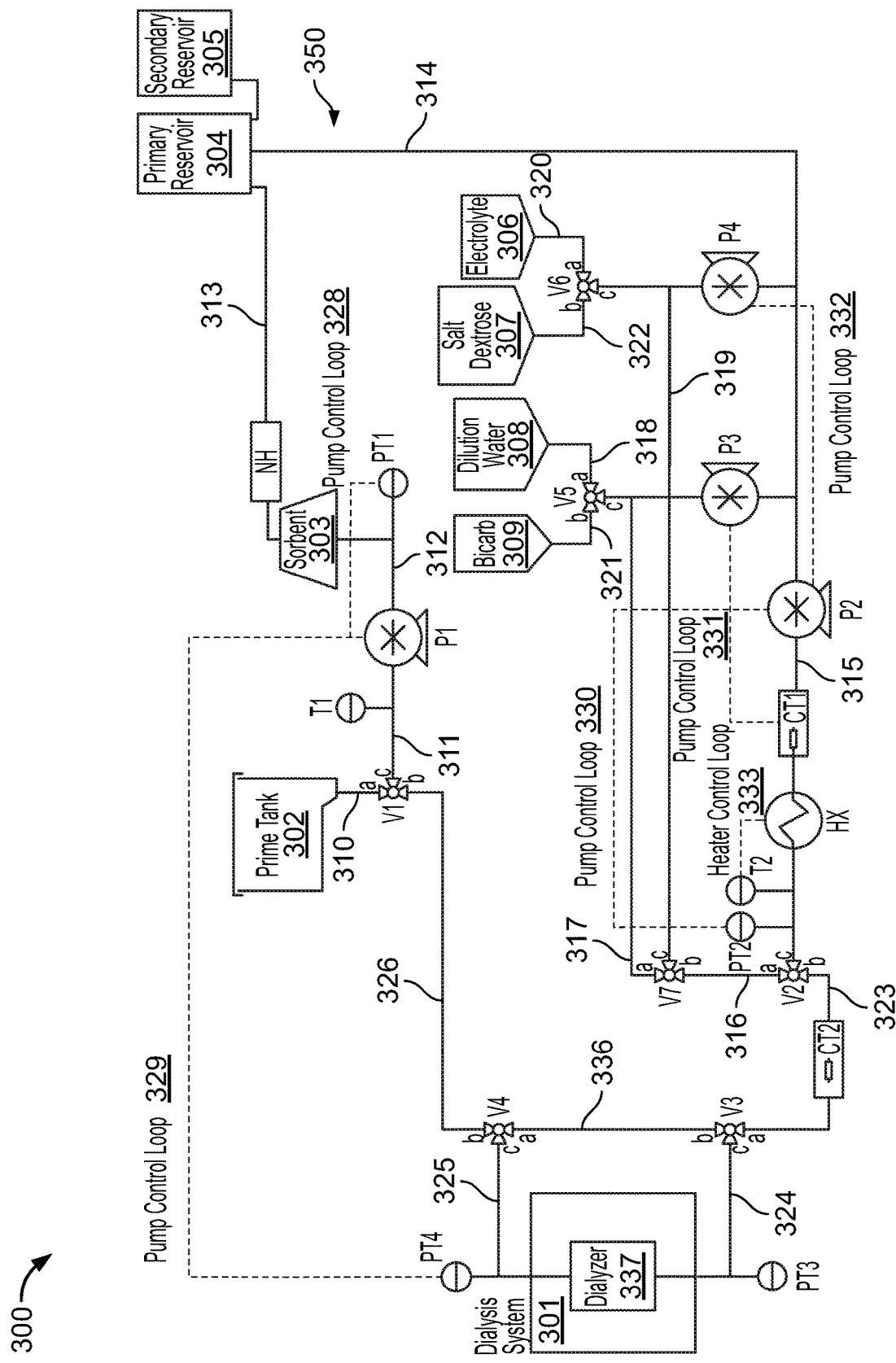
FIG. 18 provides an operational diagram by which the fluid conditioning system of FIG. 1 can cooperate with a dialysis system to form a fluid circuit for carrying out the fluid conditioning cycle.
Figure 19:
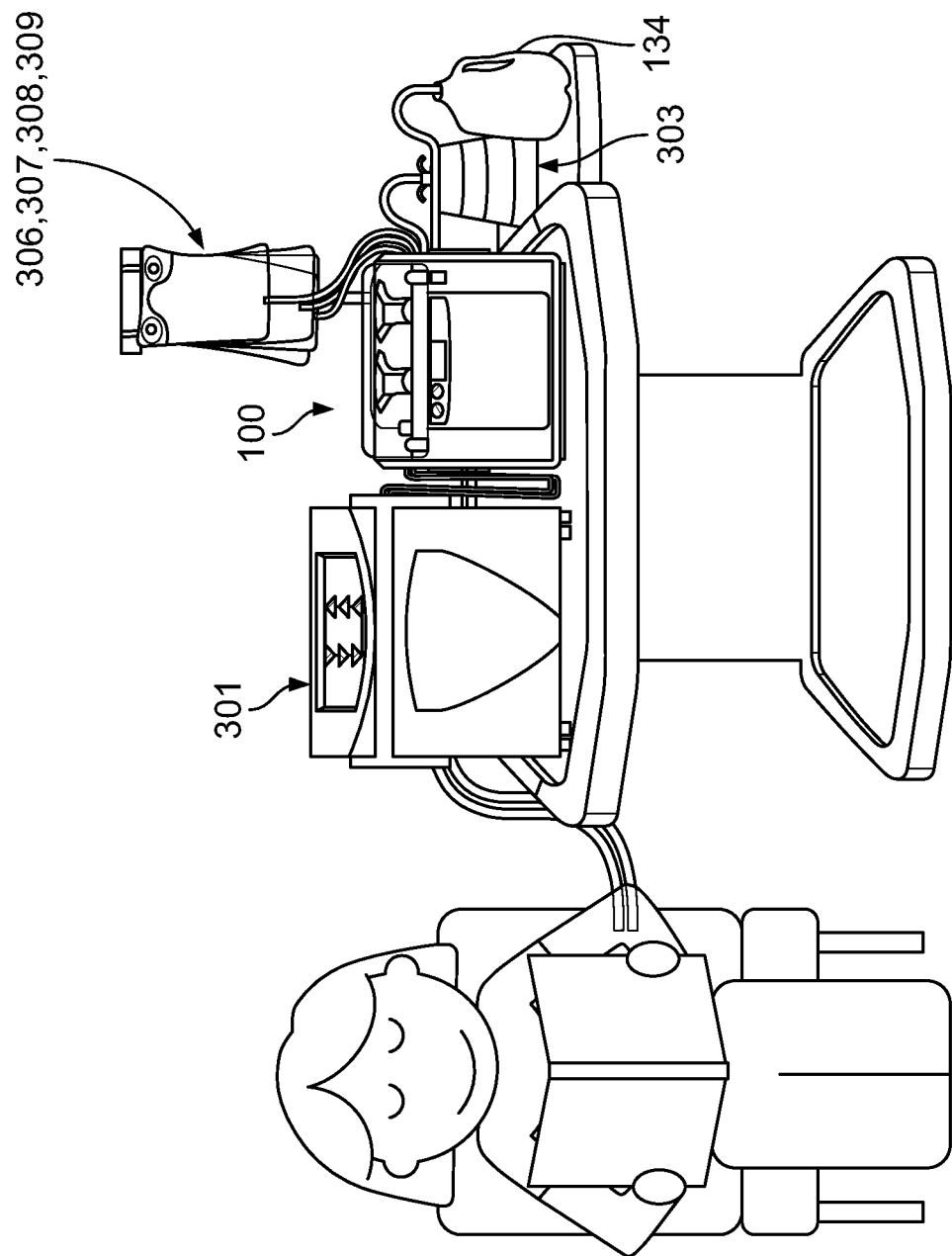
FIG. 19 illustrates an example setup of the fluid conditioning system of FIG. 1 with the dialysis system of FIG. 16.

FIG. 18 illustrates an operational diagram 300 by which the fluid conditioning system 100 can cooperate with a dialyzer 337 of a dialysis system 301 to form the fluid circuit 350 (indicated by solids lines) for carrying out a fluid conditioning cycle, while FIG. 19 illustrates an example setup of the fluid conditioning system 100 with the dialysis system 301. Example types of dialysis systems 301 that may be coupled to the fluid conditioning system 100 include HD systems, PD systems, HF systems, and HDF systems. The fluid circuit 350 incorporates components of the fluid cassette 102, as well as various other components of the fluid conditioning system 100.

For example, in addition to the components discussed above with respect to FIGS. 1-17, the fluid conditioning system 100 also includes a control system 161 (e.g., including the circuit boards 135, 159, as well as additional circuit boards for sensor circuitry) for controlling various operations of the fluid conditioning system 100 and several other, peripheral components positioned along the fluid circuit 350. These components include a prime tank 302 for collecting water to produce dialysate (e.g., sometimes referred to as dialysis fluid), a sorbent cartridge 303 for filtering tap water to provide purified water suitable for creating dialysate and for cleansing dialysate exiting the dialysis system 301, a primary reservoir 304 for collecting fluid (e.g., unconditioned water or dialysate) exiting the sorbent cartridge 303, a secondary reservoir 305 for collecting fluid that exceeds a capacity of the primary reservoir 304, a bag 306 for containing an electrolyte solution, a bag 307 for containing a salt-dextrose (SD) solution, a bag 308 for containing dilution water (DW), and a bag 309 for containing a bicarbonate (BC) solution that are positioned along the fluid flow path arrangement 300.

The bags 306, 307, 309 are pre-loaded with appropriate amounts of dry chemicals that can be dissolved in water to produce the electrolyte solution, the salt-dextrose solution, and the bicarbonate solution. Each bag 306, 307, 309 includes a nozzle that is designed to increase a velocity of a fluid flow entering the bag 306, 307, 309 and to create turbulence needed for adequate mixing and dissolution of the dry chemicals in water.

Table 1 lists approximate capacities of the various fluid-containing components of the fluid conditioning system 100.

TABLE 1

Capacities of fluid-containing components of the fluid conditioning system 100.

| Component | Capacity (mL) |
| --- | --- |
| Prime Tank (302) | 8,000 |
| Primary Reservoir (304) | 7,500 |
| Secondary Reservoir (305) | 4,500 |
| Electrolyte Bag (306) | 500 |
| Salt/Dextrose Bag (307) | 160 |
| Dilution Water Bag (308) | 4,000 |
| Bicarbonate Bag (309) | 1,000 |

The three-way valves 202 of the fluid cassette 102 are indicated as V1-V7 in the fluid circuit 350. Each valve includes three fluid ports (a), (b), (c) by which a flow path in the valve can be adjusted. A valve may be referred to as closed when two or three of its ports are closed and may be referred to as open when two or three of its ports are open. The valves include a prime valve V1, a dissolution valve V2, a bypass out valve V3, a bypass in valve V4, a BC/DW valve V5, an S/D/Electrolyte valve V6, and a fluid selector valve V7 The fluid lines 201 of the fluid cassette 102 will be referenced individually further below with respect to an operation of the fluid conditioning system 100. The high-capacity pumps 103 and the low-capacity pump 104 of the fluid conditioning system 100 are indicated respectively as P1, P2 and P3, P4 in the fluid circuit 350. The pumps include a cassette-in pump P1, a dialysate pump P2, a conductivity control pump P3, and an electrolyte/salt-dextrose pump P4. Table 2 lists approximate operational (e.g., fluid flow rate) ranges of the pumps P1-P4.

TABLE 2

Operational ranges of pumps of the fluid conditioning system 100.

| Pump | Operational Range (mL/min) |
| --- | --- |
| P1 | 20-600 |
| P2 | 20-600 |
| P3 | 0.5-90 |
| P4 | 0.5-90 |

The heater assembly 151 and the ammonia sensor 165 of the fluid conditioning system 100 are respectively indicated as a heat exchanger HX and an ammonia sensor NH in the fluid circuit 350. The conductivity sensors 203 of the fluid cassette 102 are indicated as a conductivity sensor CT1 associated with a fluid temperature upstream of the heat exchanger HX and a conductivity sensor CT2 associated with a fluid temperature downstream of the heat exchanger HX. In addition to having a capability to measure fluid conductivity, conductivity sensors CT1 and CT2 also have a capability to measure fluid temperature. Given that conductivity changes with temperature, the temperatures measured by the conductivity sensors CT1 and CT2 may, in some implementations, be used to correct conductivity values measured by the conductivity sensors CT1 and CT2 to provide temperature-compensated conductivity measurements. In some implementations, a fluid temperature measured by the conductivity sensor CT2 may also provide a safety check on a final temperature of dialysate that exits the fluid conditioning system 100 to flow into the dialysis system 303. The temperature sensors 120 of the fluid conditioning system 100 are indicated as a cassette-in temperature sensor T1 and a heat exchanger temperature sensor T2 in the fluid circuit 350. The pressure transducers 119 of the fluid conditioning system 100 are indicated as pressure transducers PT1, PT2, PT3, and PT4 in the fluid circuit 350.

The fluid conditioning system 100 can be operated in multiple stages to cooperate with the dialysis system 301 (e.g., with the dialyzer 337) for carrying out a fluid conditioning cycle in which a dialysis treatment is administered to a patient via the dialysis system 301. For example, the fluid conditioning cycle includes a priming stage, an infusion stage, and a treatment stage. The fluid conditioning cycle typically has a total duration of about 135 min to about 300 min.

Figure 20:
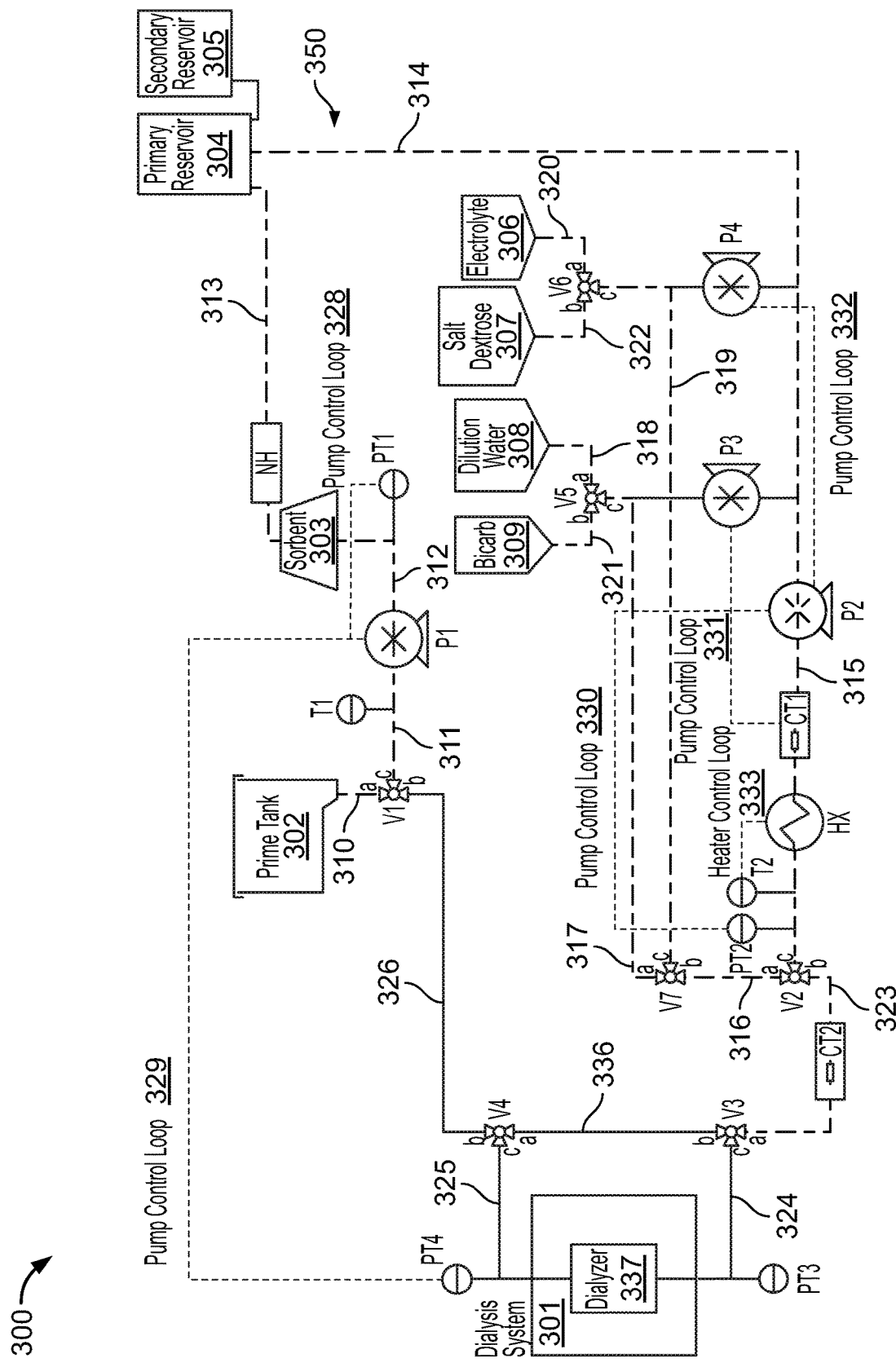
FIG. 20 illustrates a fluid flow path (indicated by highlighted fluid lines) of a priming stage of the fluid conditioning cycle carried out via the fluid circuit of FIG. 16.

FIG. 20 illustrates operation of the fluid conditioning system 100 during the priming stage, in which an initial volume of water is drawn into the fluid circuit 350 for subsequent creation of dialysate. At the beginning of the priming stage, the prime tank 302 is filled to about 7.6 L with water (e.g., tap water, bottled water, reverse osmosis water, distilled water, or drinking water) from a water source (e.g., a container 134 of water, shown in FIG. 19), pump P1 is turned on, and heat exchanger HX is turned on. The water is pumped by pump P1 from the prime tank 302 into a fluid line 310, through ports (a) and (c) of valve V1, into a fluid line 311, past temperature sensor T1, and into pump P1. At this stage of operation, pump P1 pumps water at a flow rate in a range of about 200 mL/min to about 600 mL/min, and heat exchanger HX is powered to maintain a fluid temperature at a set point in a range of about 15° C. to about 42° C.

If temperature sensor T1 detects a water temperature of greater than about 42° C., then a message is displayed on the display screen 148 to advise a user that the water temperature is too warm, valve V1 is closed, and pump P1 is turned off to prevent additional water from entering the fluid circuit 350. If temperature sensor T1 detects a water temperature of less than or equal to about 42° C., then ports (a) and (c) of valve V1 remain open, and pump P1 pumps the water through a fluid line 312 into the sorbent cartridge 303, into a fluid line 313, past ammonia sensor NH, and into the primary reservoir 304. At this stage of operation, the sorbent cartridge 303 purifies the water circulating in the fluid circuit 350, such that the water meets or exceeds water quality standards for drinking water as set by the Environmental Protection Agency (EPA) and water quality standards for hemodialysis water as set by the Association for the Advancement of Medical Instrumentation (AAMI) standard.

Once the primary reservoir 304 collects about 100 mL to about 500 mL of water, then pump P2 is turned on and pumps water into a fluid line 314, through pump P2, into a fluid line 315, past conductivity sensor CT1, and past the heat exchanger HX1, which heats the water in the fluid line 315 to the set point temperature. Pump P2 is controlled to pump water at a flow rate that is about equal to the flow rate at which water is pumped by pump P1. Water moves from the fluid line 315 through ports (c) and (a) of valve V2, into a fluid line 316, through ports (b) and (a) of valve V7, into a fluid line 317, through ports (c) and (a) of valve V5, into a fluid line 318, and further into the bag 308 until the bag 308 is filled to about 3.5 L to about 4.0 L with water (e.g., dilution water).

Next, ports (a) and (c) of valve V5 are closed, port (a) of valve V7 is closed, and port (c) of valve V7 is opened such that the pump P2 pumps water into a fluid line 319, through ports (c) and (a) of valve V6, into a fluid line 320, and further into the bag 306 until the bag 306 is filled to capacity with water to produce the electrolyte solution. Ports (a) and (c) of valve V6 are closed, port (c) of valve V7 is closed, port (a) of valve V7 is reopened, and ports (b) and (c) of valve V5 are opened. Pump P2 then pumps water into the fluid line 317, through ports (c) and (b) of valve V5, into a fluid line 321, and further into the bag 309 until the bag 309 is filled to capacity with water to produce the bicarbonate solution.

At this point in the priming stage, the set point temperature of the heat exchanger HX is increased to a range of about 31° C. to about 39° C. (e.g., where 39° C. is the maximum temperature achievable by heat exchanger HX), and the flow rate of pump P2 is reduced to a value within a range of about 100 mL/min to about 300 mL/min to increase an exposure time of the water within the heat exchanger HX for achieving the higher set point temperature. Ports (b) and (c) of valve V5 are closed, port (a) of valve V7 is closed, port (c) of valve V7 is opened, and ports (b) and (c) of valve V6 are opened. Accordingly, pump P2 pumps water into the fluid line 319, though ports (c) and (b) of valve V6, into a fluid line 322, and further into the bag 307 until the bag 307 is filled to capacity to produce the salt-dextrose solution. The higher set point temperature of heat exchanger HX facilitates dissolution of the salt-dextrose substance with the water flowing into the bag 309. At this point during the fluid conditioning cycle, the priming stage concludes, the prime tank 302 has substantially emptied, the pumps P1, P2 are turned off and the infusion stage can begin. The priming stage typically lasts a duration of about 10 min to about 30 min (e.g., about 20 min).

Figure 21:
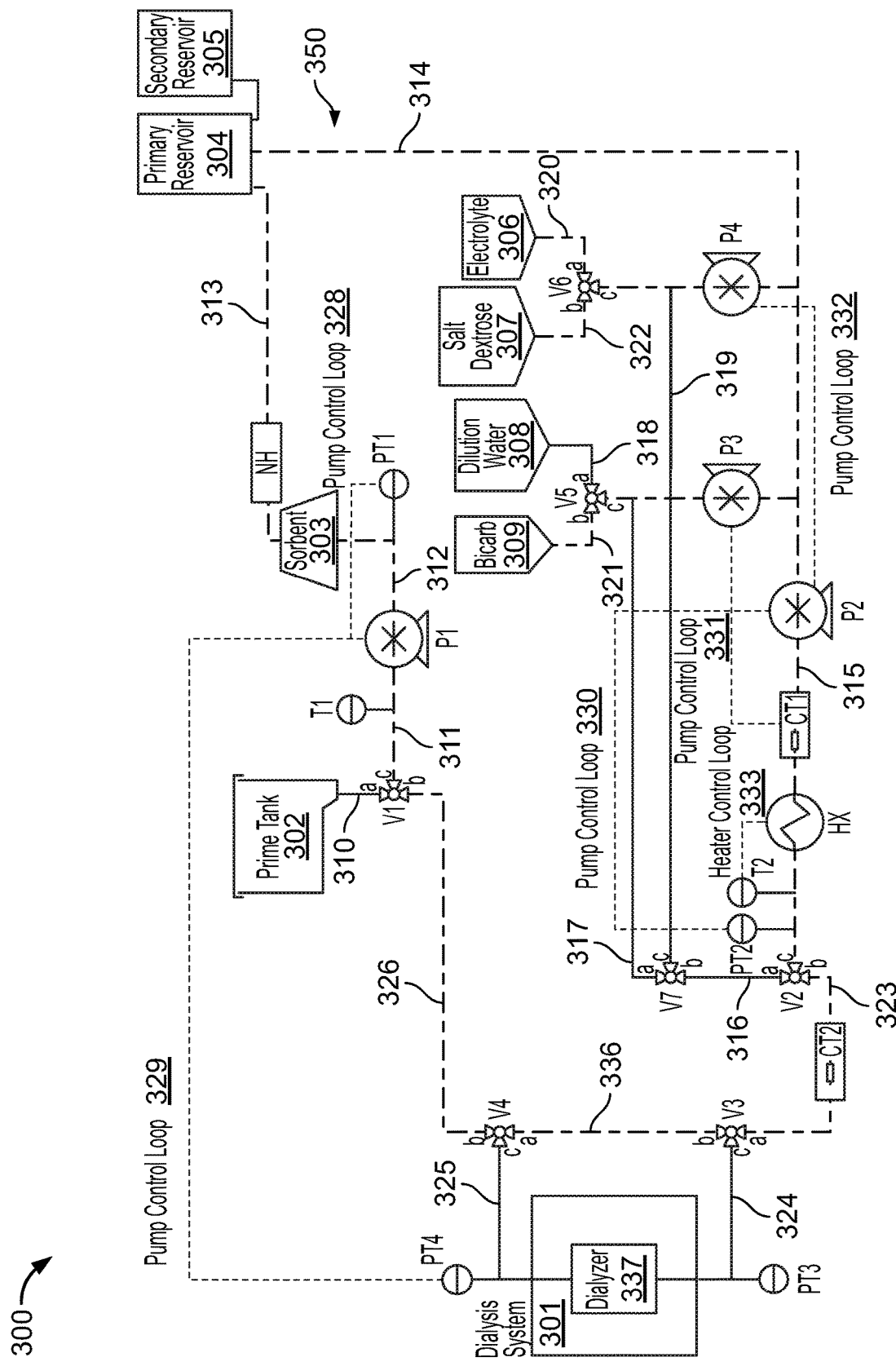
FIG. 21 illustrates a fluid flow path (indicated by highlighted fluid lines) of an infusion stage of the fluid conditioning cycle carried out via the fluid circuit of FIG. 16.

FIG. 21 illustrates operation of the fluid conditioning system 100 during the infusion stage, in which bicarbonate, salt, and dextrose are added to the water in the fluid circuit 350 to produce dialysate. In particular, bicarbonate, salt, and dextrose are added to the water in a controlled manner (e.g., under flow rate control) until the salt and dextrose reach physiologically acceptable concentrations and until the bicarbonate yields a physiologically acceptable fluid conductivity and fluid pH. During the infusion stage, heat exchanger HX is powered to maintain a fluid temperature at a set point in a range of about 35° C. to about 39° C.

At the beginning of the infusion stage, valve V7 is closed, port (a) of valve V2 closes, port (b) of valve V2 opens, ports (a) and (b) of both valves V3 and V4 open, port (b) of valve V1 opens, port (a) of valve V1 closes, ports (b) and (c) of valve V6 remain open, and ports (b) and (c) of valve V5 open. Pumps P1, P2 immediately turn on to pump water at a flow rate in a range of about 300 mL/min to about 600 mL/min within the fluid circuit 350. At the same time, pumps P3 and P4 are turned on. Pump P3 pumps bicarbonate solution out of the bag 309 at a flow rate of about 10 mL/min to about 100 mL/min, into the fluid line 317, through the pump P3, and into the fluid line 314. Pump P4 pumps salt-dextrose solution out of the bag 307 at a variable flow rate into the fluid line 319, through pump P4, and into the fluid line 314. The flow rate at which P4 initially pumps fluid is in a range of about 1 mL/min to about 100 mL/min. The flow rate is gradually stepped down by a factor of 2 at periodic time increments of about 1 min. The flow rates of pumps P3 and P4 are set to completely add the infusion volume respectively of the BC solution and the SD solution over a single revolution around the fluid circuit 350. Accordingly, the flow rates of pumps P3 and P4 depend on the flow rates of pumps P1 and P2 during the infusion stage. For example, if the flow rates of pumps P1 and P2 are set to 200 mL/min, then the flow rates of pumps P3 and P4 will be relatively slow. Conversely, if the flow rates of pumps P1 and P2 are set to 600 mL/min, then the flow rates of pumps P3 and P4 will be relatively fast.

Once the bag 307 empties of the salt-dextrose solution, port (b) of valve V6 closes, and port (a) of valve V6 opens to allow pump P4 to pump the electrolyte solution out of the bag 306 at a flow rate of about 0.5 mL/min to about 5 mL/min into the fluid line 314. Once the electrolyte solution reaches valve V3, the infusion stage concludes, and the treatment stage can begin. However, if the treatment stage does not begin immediately, the fluid conditioning system 100 can be operated to continue to circulate dialysate around the fluid circuit 350 through fluid lines 311, 312, 313, 314, 315, 323, 336, 326 or to allow the dialysate to remain static (e.g., without circulation) until the treatment stage begins. The infusing stage typically lasts a duration of about 5 min to about 6 min.

Figure 22:
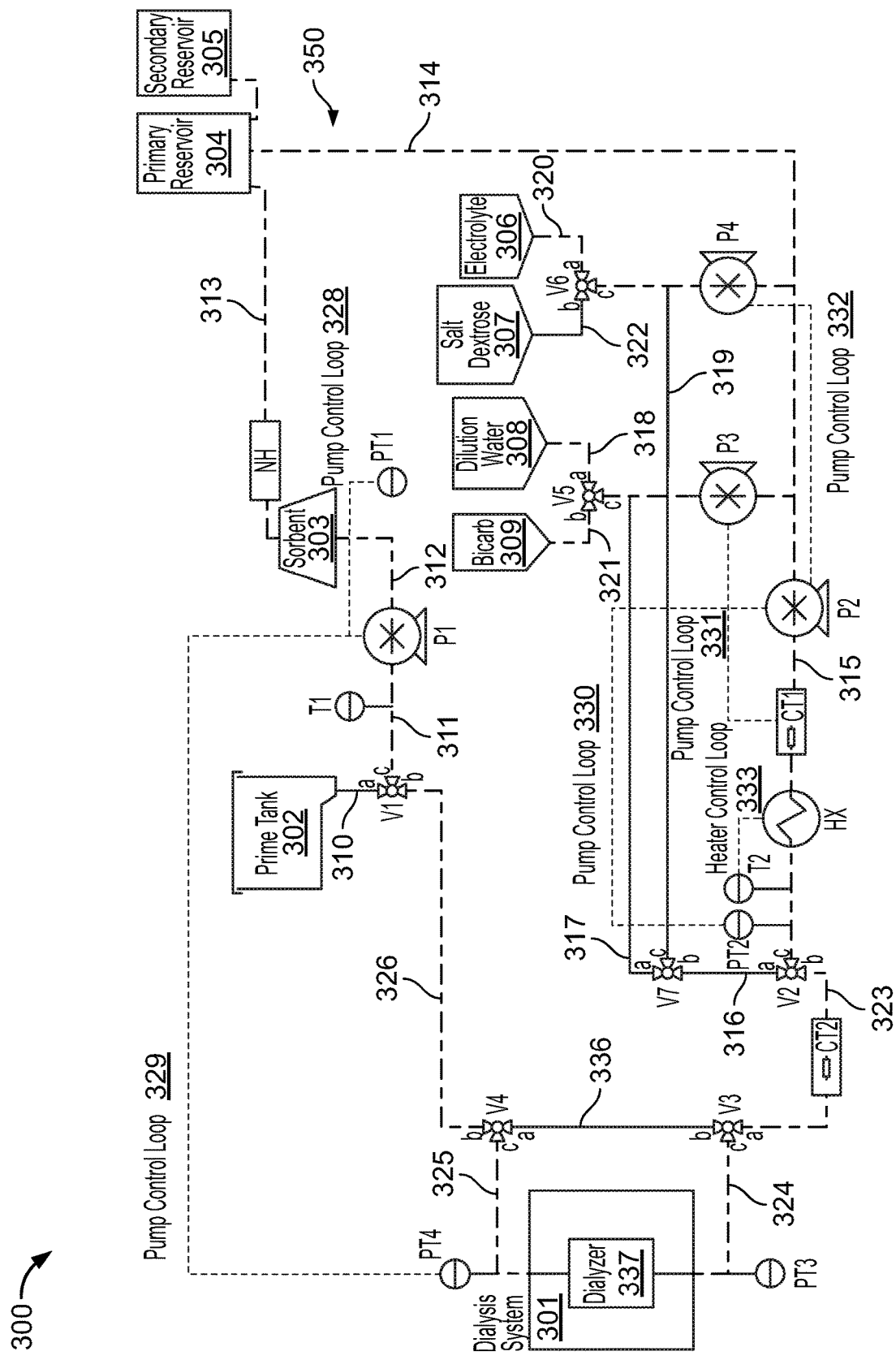
FIG. 22 illustrates a fluid flow path (indicated by highlighted fluid lines) of a treatment stage of the fluid conditioning cycle carried out via the fluid circuit of FIG. 16.

FIG. 22 illustrates operation of the fluid conditioning system 100 during the treatment stage, in which bicarbonate, salt, and dextrose are added to the water in the fluid circuit 350 to produce dialysate. The treatment stage includes a first phase in which bicarbonate solution is used to regulate a conductivity of the dialysate and a second phase in which dilution water is used to regulate a conductivity of the dialysate. Pumps P1, P2 pump dialysate at a flow rate in a range of about 200 mL/min to about 600 mL/min. The set point temperature of heat exchanger HX is maintained at a physiologically acceptable temperature in an acceptable range of about 35° C. to about 39° C. (e.g., about 37° C.), as specifically selected by a user of the fluid conditioning system 100 to suit patient comfort. At any point during the treatment stage, if the dialysate fluid temperature measured at CT2 is outside of a range of about 35° C. to about 42° C., then the fluid conditioning system 100 will enter a bypass mode in which dialysate will flow through fluid line 336 to bypass flow through the dialysis system 301 via fluid lines 324, 325. While the fluid conditioning system 100 is operating in the bypass mode, a message will be displayed on the display screen 148 indicating that the fluid temperature is too low or too high. The fluid conditioning system 100 will remain in bypass mode until the fluid temperature stabilizes within the acceptable range.

During the first phase of the treatment stage, port (b) of valve V3 is closed, port (c) of valve V3 is opened to allow pump P2 to pump "fresh" dialysate (e.g., cleaned, conditioned dialysate) through a fluid line 324 and into the dialysis system 301, port (a) of valve V4 is closed, and port (c) of valve V4 is opened to allow pump P1 to pump "spent"

dialysate (e.g., contaminated dialysate) through a fluid line 325 out of the dialysis system 301 and further into a fluid line 326. Accordingly, a bypass fluid line 336 that extends between valves V3, V4 is closed. During the treatment stage, spent dialysate is infused with ultra-filtrate from the patient's blood within the dialysis system 301. The ultra-filtrate carries toxic substances, such as urea, all of the small water-soluble uremic toxins, and other toxic substances (e.g., guanidosuccinic acid, methylguanidine, 1-methyladenosine, 1-methylinosine, N2,N2-dimethylguanosine, pseudouridine, arab(in)itol, mannitol, α-N-acetylarginine, orotidine, oxalate, guanidine, erythritol, creatine, orotic acid, phenylacetylglutamine, creatinine, myoinositol, γ-guanidinobutyric acid, β-guanidinopropionic acid, symmetric dimethyl-arginine (SDMA), asymmetric dimethyl-arginine (ADMA), sorbitol, uridine, and xanthosine).

From the fluid line 326, the spent dialysate is pumped through ports (b) and (c) of valve V1, the fluid line 311, pump P1, the fluid line 312, and into the sorbent cartridge 303. Within the sorbent cartridge 303, the toxic substances are removed from (e.g., filtered out of) the spent dialysate to produce "regenerated" dialysate (e.g., cleaned, unconditioned dialysate) that flows out of the sorbent cartridge 303 and into the fluid line 313, past the ammonia sensor NH, and into the primary reservoir 304. In some cases, a volume of the regenerated dialysate within the primary reservoir 304 exceeds a capacity of the primary reservoir 304 and therefore flows through a fluid line 327 into the secondary reservoir 305, which remains in fluid communication with the primary reservoir 304 throughout the treatment stage. Pump P2 pumps regenerated dialysate out of the primary reservoir 304, into the fluid line 314, and into pump P2. While the regenerated dialysate exiting the sorbent cartridge 303 has been stripped of toxic substances that were absorbed from the patient's blood in the dialysis system 301, the regenerated dialysate must be further conditioned to meet acceptable physiological properties before being circulated back into the dialyzer 337 of the dialysis system 301 as fresh dialysate.

Accordingly, pump P4 continues to pump the electrolyte solution out of the bag 306 and into the fluid line 320, through ports (a) and (c) of valve V6, into an upper segment of the fluid line 319, through pump P4, and into the fluid line 314 at a flow rate that depends on (e.g., is a fraction of) the flow rate at which pump P2 pumps dialysate. Thus, pumps P2, P4 together form a closed pump control loop 332 that governs the flow rate at which pump P4 pumps the electrolyte solution, which is in a range of about 0.5 mL/min to about 5 mL/min. Furthermore, pump P3 continues to pump either the bicarbonate solution out of the bag 309 or the dilution water out of the bag 308, through port (c) of valve V5, into an upper segment of the fluid line 317, through pump P3, and into the fluid line 314 to further condition the dialysate.

As the dialysate passes through pump P2 and conductivity sensor CT1, the conductivity sensor CT1 detects a conductivity of the dialysate. Based on continuous measurements of the conductivity of the dialysate, either the bicarbonate solution or the dilution water will be continuously selected for addition to the dialysate through port (c) of valve V5, and the flow rate at which pump P3 pumps dialysate will be continuously adjusted to maintain a conductivity of the dialysate within a physiologically acceptable range of 13.5 mS/cm to 14.2 mS/cm. Generally, as a difference between the measured conductivity and an acceptable conductivity increases, the flow rate at which the pump P3 pumps fluid increases. Accordingly, as the difference between the measured conductivity and the acceptable conductivity decreases, the flow rate at which the pump P3 pumps fluid decreases. In this manner, the conductivity meter CT1 and the pump P3 together form a closed pump control loop 331 that regulates a flow rate at which the pump P3 pumps fluid. If the conductivity of the dialysate is too low during the first phase of the treatment stage, then bicarbonate solution is infused into the dialysate to raise the conductivity.

After passing the conductivity sensor CT1, the dialysate flows past the heat exchanger HX and temperature sensor T2. Based on a fluid temperature detected by temperature sensor T2, a power level of the heat exchanger HX will be adjusted to maintain the temperature of the dialysate at the set point temperature of the heat exchanger HX. In this way, temperature sensor T2 and heat exchanger HX form a closed heater control loop 333. The dialysate flows from the fluid line 315 through ports (c) and (b) of valve V2 into the fluid line 323 and past conductivity sensor CT2. As the dialysate passes conductivity sensor CT2, conductivity sensor CT2 performs a second check (e.g., downstream of heat exchanger HX) to detect a conductivity of the dialysate.

If the conductivity of the dialysate is outside of the acceptable range (e.g., either too low or too high), but within a predetermined range (e.g., that is broader than the acceptable range), then a safety system in electrical communication with the conductivity sensor will adjust a flow rate of infusion of the bicarbonate solution or the dilution water to achieve a conductivity within the acceptable range. If the conductivity level of the dialysate is outside of the predetermined physiologically safe range, then, in some implementations, the fluid conditioning system 100 will attempt to restore the safe fluid parameters and continue the treatment. For example, valves V3 and V4 will adjust to direct fluid through the bypass fluid line 336 and close fluid lines 324, 325 until a time at which the conductivity has again stably reached a physiologically safe range, at which time valves V3, V4 will adjust to close the bypass fluid line 336 and direct fluid to and from the dialysis system 301 via fluid lines 324, 325. In some implementations, a user may also be instructed to check that fluid levels of the bicarbonate solution and the dilution water are non-zero upon return of the conductivity to a physiologically safe range.

Over time, the sorbent cartridge 303 changes a composition of the regenerated dialysate exiting the sorbent cartridge 303 during the first phase of the treatment stage (e.g., an early, initial phase in which the patient's blood is initially circulated through the dialysis machine 301). For example, during the first phase of the treatment stage, levels of toxic substances within the spent dialysate are relatively high. The sorbent cartridge 303 converts urea into ammonium and captures the ammonium within one or more filtration layers within the sorbent cartridge 303 to remove the ammonium from the dialysate. While the filtration layers capture the ammonium, the filtration layers release sodium cations and other cations into the dialysate via cation exchange, which increases the conductivity and/or decreases the pH of the regenerated dialysate exiting the sorbent cartridge 303.

Over the course of the first phase of the treatment stage, spent dialysate entering the sorbent cartridge 303 contains fewer toxic substances (e.g., as uremic toxins are removed from the patient's blood), and the sorbent cartridge 303 releases more sodium cations. Therefore, the conductivity of the dialysate exiting the sorbent cartridge 303 gradually increases over time. Once the conductivity of the dialysate reaches a predetermined value in a range of about 13.8 mS/cm to about 14.0 mS/cm, the first phase of the treatment stage in which bicarbonate is used to regulate the conductivity of the dialysate concludes, and the second phase of the treatment stage begins.

During the second (e.g., later, final) phase of the treatment stage, bicarbonate is no longer used to regulate (e.g., increase) the conductivity of the dialysate, and dilution water is the sole substance at valve V5 that is used to regulate (e.g., decrease) the conductivity of the dialysate until the end of the treatment stage (e.g., the end of the second phase). Accordingly, port (b) of valve V5 is closed, while port (a) of valve V5 is opened. If the conductivity of the dialysate is too high during the second phase of the treatment stage, then dilution water is infused into the dialysate to lower the conductivity of the dialysate.

Over the course of the second phase of the treatment stage, an amount of ammonium captured in the sorbent cartridge 303 increases, such that a capacity of the sorbent cartridge 303 to absorb additional ammonium gradually decreases, and a level of ammonia (e.g., generated by the ammonium) within the regenerated dialysate eventually increases, once the capacity of the sorbent to adsorb ammonium is exhausted. The ammonia sensor NH detects the level of ammonia within the regenerated dialysate at a location downstream of the sorbent cartridge 303.

The treatment stage (e.g., including both the first and second phases) typically lasts a duration of about 120 min to about 300 min. For example, 240 minutes (e.g., 4 hours) is a standard duration that typically achieves adequate treatment for the vast majority of patients. Furthermore, most treatment stages will end after four hours without reaching a threshold ammonium concentration of 2 mg/dL (e.g., without ever approaching exhaustion of the filtering capabilities of the sorbent cartridge 303). The fluid conditioning system 100 will sound an audio alert signifying that the treatment completed successfully and that the patient can disconnect himself or herself from the dialyzer 337. However, if the ammonium level in the dialysate (e.g., as detected by the ammonia sensor NH) indicates that the sorbent cartridge 303 is no longer absorbing enough ammonium from the spent dialysate to maintain the ammonium level at or below an acceptable value of about 2 mg/dL prior to the standard treatment duration, then the treatment stage will conclude prematurely. Such conditions may occur occasionally for larger patients that have very high blood urea nitrogen (BUN) levels.

Once the treatment stage concludes, the fluid circuit 350 can be drained of spent dialysate, and the spent dialysate can be disposed of as waste. In some examples, the bags 306, 307, 308, 309 and the various fluid lines can be manually removed and discarded while still containing dialysate. In some examples, the patient may disconnect from the dialysis system 301 and drain the fluid lines 323, 326 to a waste receptacle to empty the various components of the fluid conditioning system 100. In some examples, the fluid conditioning system 100 may be operated to run either or both of pumps P1, P2 in a forward direction or a reverse direction to drain any of the bags 306, 307, 308, 309, the sorbent cartridge 303, the prime tank 302, the primary reservoir 304, and the secondary reservoir 305. In some examples, the fluid conditioning system 100 may be operated to run pumps P4 and P3 in a forward direction to drain the bags 306, 307 and 308, 309. In some examples, such operation of pumps P4, P3 may be carried out based on readings at conductivity meter CT1. For example, upon detection of a sufficiently low threshold conductivity, the electrolyte bag 306 may be assumed to have been emptied, such that a next bag or fluid line can be drained.

Throughout the fluid conditioning cycle, pressure transducers PT1, PT2, PT3, PT4 detect fluid pressures to regulate pump flow rates. For example, during all stages (e.g., the priming, infusion, and treatment stages) of the fluid conditioning cycle, pressure transducer PT1 forms a closed pump control loop 328 with pump P1 by detecting a fluid pressure of the dialysate within the fluid line 312 (e.g., located downstream of pump P1) and providing a feedback signal to pump P1 indicative of the fluid pressure. Based on the fluid pressure of the dialysate, an angular speed (e.g., an RPM level) of pump P1 is adjusted to maintain the flow rate within a desired range. During the treatment stage of the fluid conditioning cycle, pressure transducer PT4 forms an additional closed pump control loop 329 with pump P1 by detecting a fluid pressure of the dialysate exiting the dialysis system 301 (e.g., upstream of pump P1) and providing a forward signal to pump P1 indicative of the fluid pressure. Based on the fluid pressure of the dialysate, the angular speed of pump P1 is adjusted to closely match the flow rate at pump P1 with that of the dialysate exiting the dialysis system 301. Accordingly, the fluid pressure of the dialysate within the fluid line 312 (e.g., downstream of pump P1) is at least in part affected by the fluid pressure of the dialysate exiting the dialysis system 301 (e.g., upstream of pump P1).

Similarly, during all stages (e.g., the priming, infusion, and treatment stages) of the fluid conditioning cycle, pressure transducer PT2 forms a closed pump control loop 330 with pump P2 by detecting a fluid pressure of the dialysate within the fluid line 315 (e.g., located downstream of pump P2) and providing a feedback signal to pump P2 indicative of the fluid pressure. Based on the fluid pressure of the dialysate, an angular speed of pump P2 is adjusted to maintain the flow rate within a desired range. During the treatment stage of the fluid conditioning cycle, the flow rate at which pump P3 pumps fluid is regulated by a feedback signal from conductivity meter CT1 to form the pump control loop 331, and the flow rate at which pump P4 pumps the electrolyte solution is regulated by a feedback signal from pump P2 to form the pump control loop 332, as discussed above.

During all stages of the fluid conditioning cycle, pressure transducers PT3 and PT4 detect operation of the dialyzer 337. If measurements at pressure transducers PT3 and PT4 indicate that there is no fluid flow through the dialyzer 337, then the fluid conditioning system 100 will enter the bypass mode to flow dialysate through fluid line 336 and to avoid delivering dialysate to the dialysis system 301 via fluid lines 324, 325.

Figure 23:
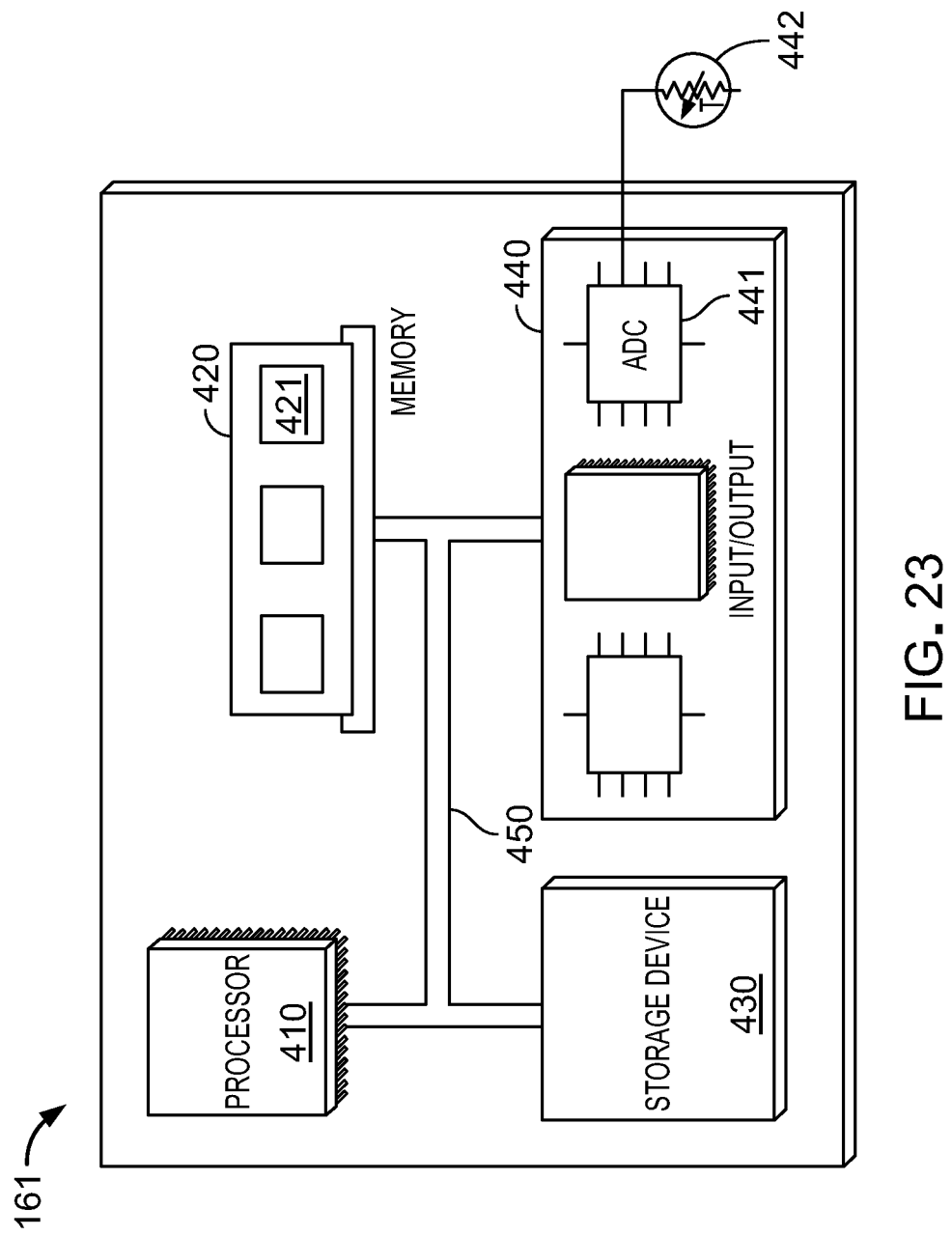
FIG. 23 provides a block diagram of a control system of the fluid conditioning system of FIG. 1.
Figure 26:
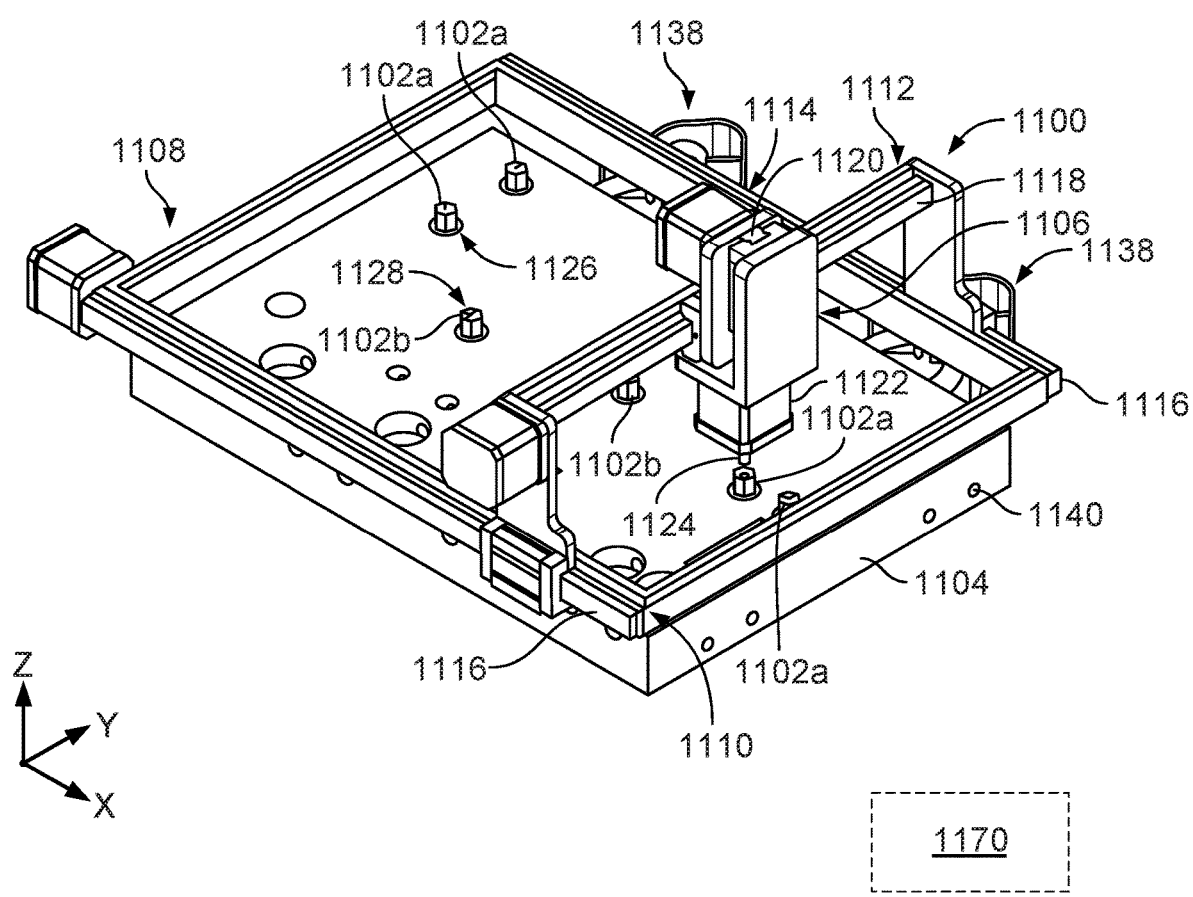
FIG. 26 is a perspective view of an actuation system designed to control multiple valves of a cassette within a dialysis system.

FIG. 23 provides a block diagram of the control system 161. The control system 161 includes a processor 410, a memory 420, a storage device 430, and an input/output interface 440. In some embodiments, the control system 161 includes more than one processor 410, memory 420, storage device 430, and/or input/output interface 440. Each of the components 410, 420, 430, and 440 can be interconnected, for example, using a system bus 450. The processor 410 is capable of processing instructions for execution within the control system 161. The processor 410 can be a single-threaded processor, a multi-threaded processor, or a quantum computer. The processor 410 is capable of processing instructions stored in the memory 420 or on the storage device 430.

The memory 420 stores information within the control system 161. In some implementations, the memory 420 is a computer-readable medium. The memory 420 can, for example, be a volatile memory unit or a non-volatile memory unit. The storage device 430 is capable of providing mass storage for the control system 139. In some implementations, the storage device 430 is a non-transitory computer-readable medium. The storage device 430 can include, for example, a hard disk device, an optical disk device, a solid-state drive, a flash drive, magnetic tape, or some other large capacity storage device. The storage device 430 may alternatively be a cloud storage device, e.g., a logical storage device including multiple physical storage devices distributed on a network and accessed using a network.

The input/output interface 440 provides input/output operations for the control system 161. In some implementations, the input/output interface 440 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices (e.g., the display screen 148). In some implementations, mobile computing devices, mobile communication devices, and other devices are used.

In some implementations, the input/output interface 440 includes at least one analog-to-digital converter 441. An analog-to-digital converter converts analog signals to digital signals, e.g., digital signals suitable for processing by the processor 410. In some implementations, one or more sensing elements are in communication with the analog-to-digital converter 441, as will be discussed in more detail below.

In some implementations, the control system 161 is a microcontroller. A microcontroller is a device that contains multiple elements of a computer system in a single electronics package. For example, the single electronics package could contain the processor 410, the memory 420, the storage device 430, and input/output interfaces 440.

FIGS. 24 and 25 provide block diagrams of a hardware system 500 and a software system 600 of the fluid conditioning system 100 that are provided by the control system 161. As shown in FIG. 24, the hardware system 500 is provided by a circuit board for generating GUIs for display on the display screen 148 and one or more circuit boards 135 for controlling the electromechanical peripheral components of the fluid conditioning system 100, and the various electromechanical peripheral components. The software system 600 can be broken down into an external view 610, an application layer 620, and a driver layer 630. The external view 610 includes user interfaces provided by the GUIs, lights, sounds, and debug ports. The application layer 620 includes business logic, and the driver layer 630 is configured to implement peripheral-specific code (e.g., communication protocols and stepper motor drivers).

Other embodiments are also possible. For example, FIGS. 26-30 illustrate various configurations of an actuation system 1100 that is designed to control multiple valves 1102 (e.g., valves 1102a, 1102b) of a cassette 1104 (e.g., a fluid cassette) within a dialysis system for carrying out a dialysis treatment. In the example actuation system 1100, the valves 1102 may be embodiments of the valves 200 of the fluid conditioning system 100, the cassette 1104 may be an embodiment of the fluid cassette 102 of the fluid conditioning system 100, and such dialysis system may be embodied as the fluid conditioning system 100. The actuation system 1100 includes a drive unit 1106 and a positioning frame 1108 along which the drive unit 1106 can be moved to engage a selected valve 1102. The drive unit 1106 and the positioning frame 1108 may be controlled by a control unit (e.g., illustrated schematically as a control unit 1170 in FIG. 26). In some embodiments, the control unit 1170 may be implemented as part of the control system 161 of the fluid conditioning system 100. In some embodiments, the drive unit 1106 may provide an embodiment of one or more of the drive unit 130, the motor 129, and the actuator 125 of the fluid conditioning system 100 or may be included in a fluid conditioning system instead of one or more of the drive unit 130, the motor 129, and the actuator 125.

The positioning frame 1108 of the actuation system 1100 is an xyz table that provides 3 degrees of freedom for the drive unit 1106 along the cassette 1104. For example, the positioning frame 1108 includes a first rail 1110 that allows the drive unit 106 to be moved along an x-axis, a second rail 1112 that allows the drive unit 1106 to be moved along a y-axis, and a third rail 1114 that allows the drive unit 1106 to be moved along a z-axis. The first rail 1110 includes two shafts 1116 extending along opposite sides of the cassette 1104 and along which the second rail 1112 can slide horizontally for movement of the drive unit 1106 in the x-direction. For example, FIGS. 27-29 show the second rail 1112 located at three different positions along the x-axis. The second rail 1112 includes a shaft 1118 spanning the cassette 1104 and along which the third rail 1114 can slide horizontally for movement of the drive unit 1106 in the y-direction. The third rail 1114 includes a shaft 1120 extending vertically above the cassette 1104 and along which the drive unit 1106 can slide vertically for movement of the drive unit 1106 in the z-direction.

In some embodiments, the first rail 1110 can typically be fully traversed by the second rail 1112 in about 0.5 seconds to about 1.0 seconds. In some embodiments, the second rail 1112 can typically be fully traversed by the third rail 1114 in about 0.5 seconds to about 1.0 seconds. In some embodiments, the third rail 1114 can typically be fully traversed by the drive unit 1106 in about 0.5 seconds to about 1.0 seconds. Accordingly, the positioning frame 1108 and the drive unit 1106 can be controlled such that the drive unit 1106 can completely traverse the first, second, and third linear rails 1110, 1112, 1114 in a total time of up to about 0.5 seconds to about 1.0 seconds.

The drive unit 1106 includes a support base 1122 and an actuator 1124 that extends from the support base 1122. The actuator 1124 is formed to engage complementary portions of the valves 1102 such that movement of the actuator 1124 causes movement of a respective valve 1102. Once an xy position of the drive unit 1106 has been aligned (e.g., centered) with a selected valve 1102 (e.g., as governed by the control unit of the dialysis system), the drive unit 1106 can be lowered to engage the valve 1102 and subsequently rotated to actuate (e.g., open or close) the valve 1102.

For example, while engaged with a valve 1102, the actuator 1124 can be rotated such that the actuator 1124 applies a force to the valve 1102 to rotate the valve 1102 to a selected orientation that communicates an internal channel of the valve 1102 with an adjacent fluid path to open the valve 1102 (e.g., thereby allowing passage of fluid) or that closes off an adjacent fluid path to close the valve 1102 (e.g., thereby preventing passage of fluid). Furthermore, the control unit 1170 of the dialysis system can include an encoder that monitors a rotational position of the actuator 1124.

Figure 31:
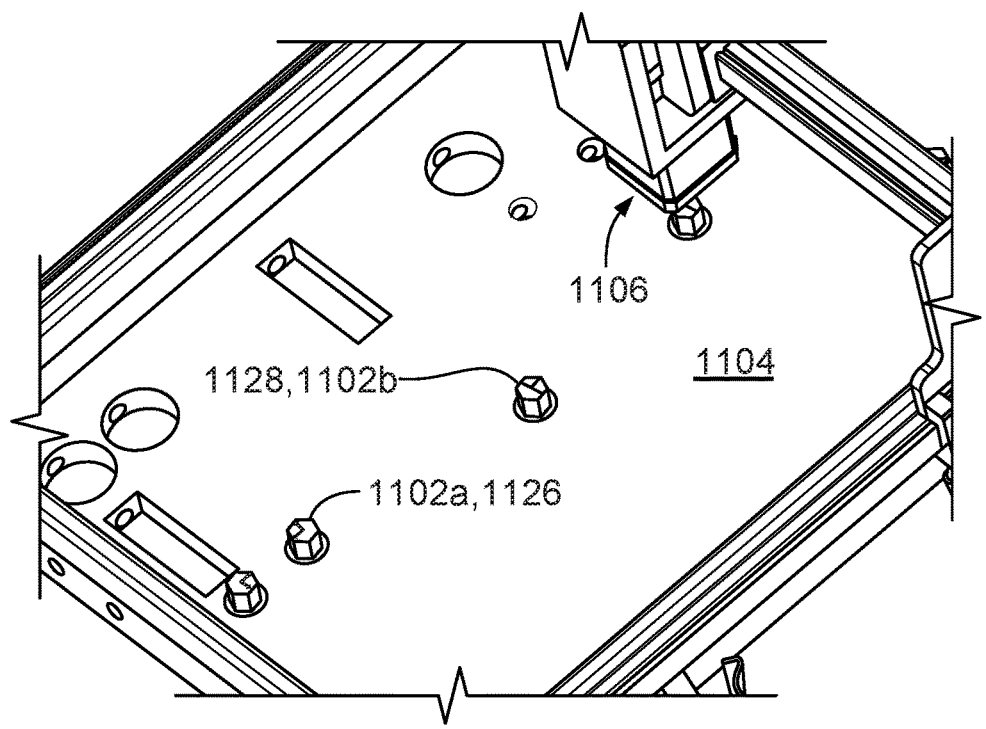
FIG. 31 is an enlarged perspective view of valves that can be controlled by the actuation system of FIG. 26.
Figure 32:
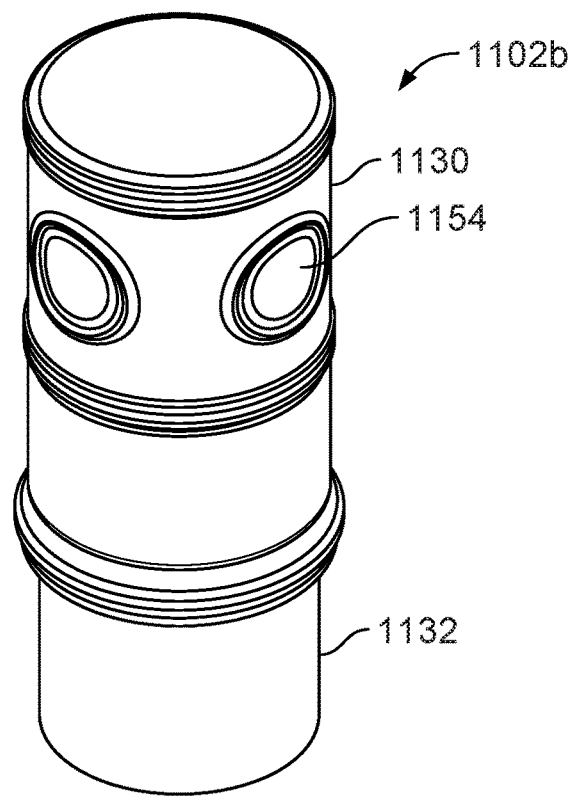
FIG. 32 is a perspective view of a valve that can be controlled by the actuation system of FIG. 26.
Figure 33:
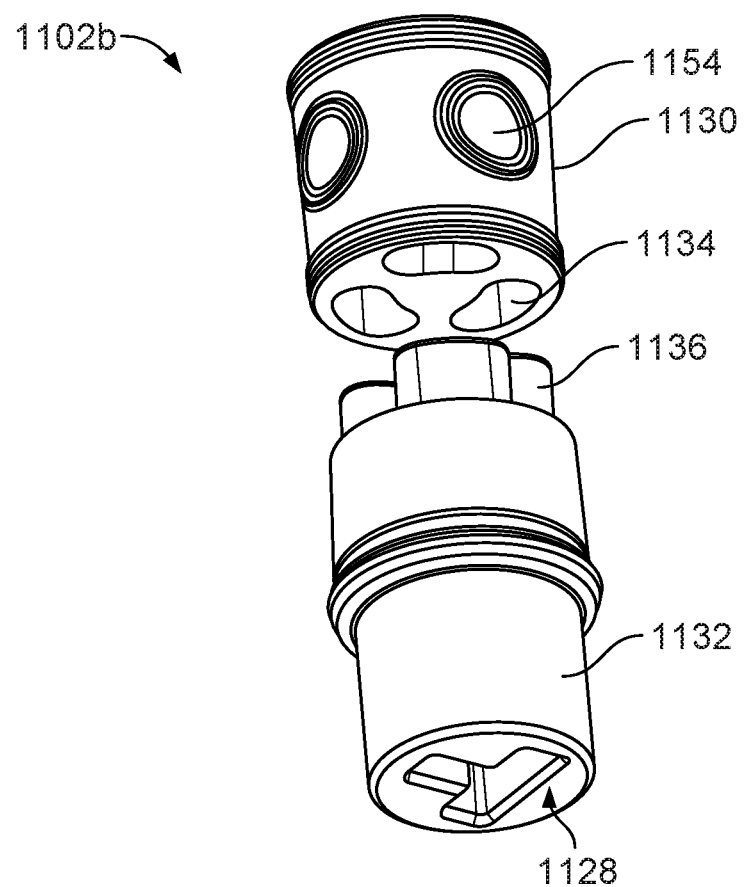
FIG. 33 is an exploded perspective view of the valve of FIG. 32.

Referring to FIG. 31, the example cassette 1104 includes six valves 1102 that are located along various fluid paths defined by the cassette 1104. Four valves 1102a are two-way valves, as indicated by a key 1126, and two valves 1102b are three-way valves, as indicated by a key 1128. Referring to FIGS. 32 and 33, each valve 1102 includes a valve body 1130 defining internal channeling 1154 through which fluid can flow and a valve stem 1132 defining a key 1126 or a key 1128 with which the actuator 1124 can be engaged to move the valve 1102. As shown in FIG. 33, the valve body 1130 defines multiple recesses 1134, and the valve stem 1132 defines multiple protrusions 1136 that extend respectively within the recesses 1134 to couple the valve stem 1132 to the valve body 1130. The valve bodies 1130 are disposed within a boundary of the cassette 1104, while the valve stems 1132 extend away from the cassette 1104 for exposure to the actuator 1124.

Figure 30:
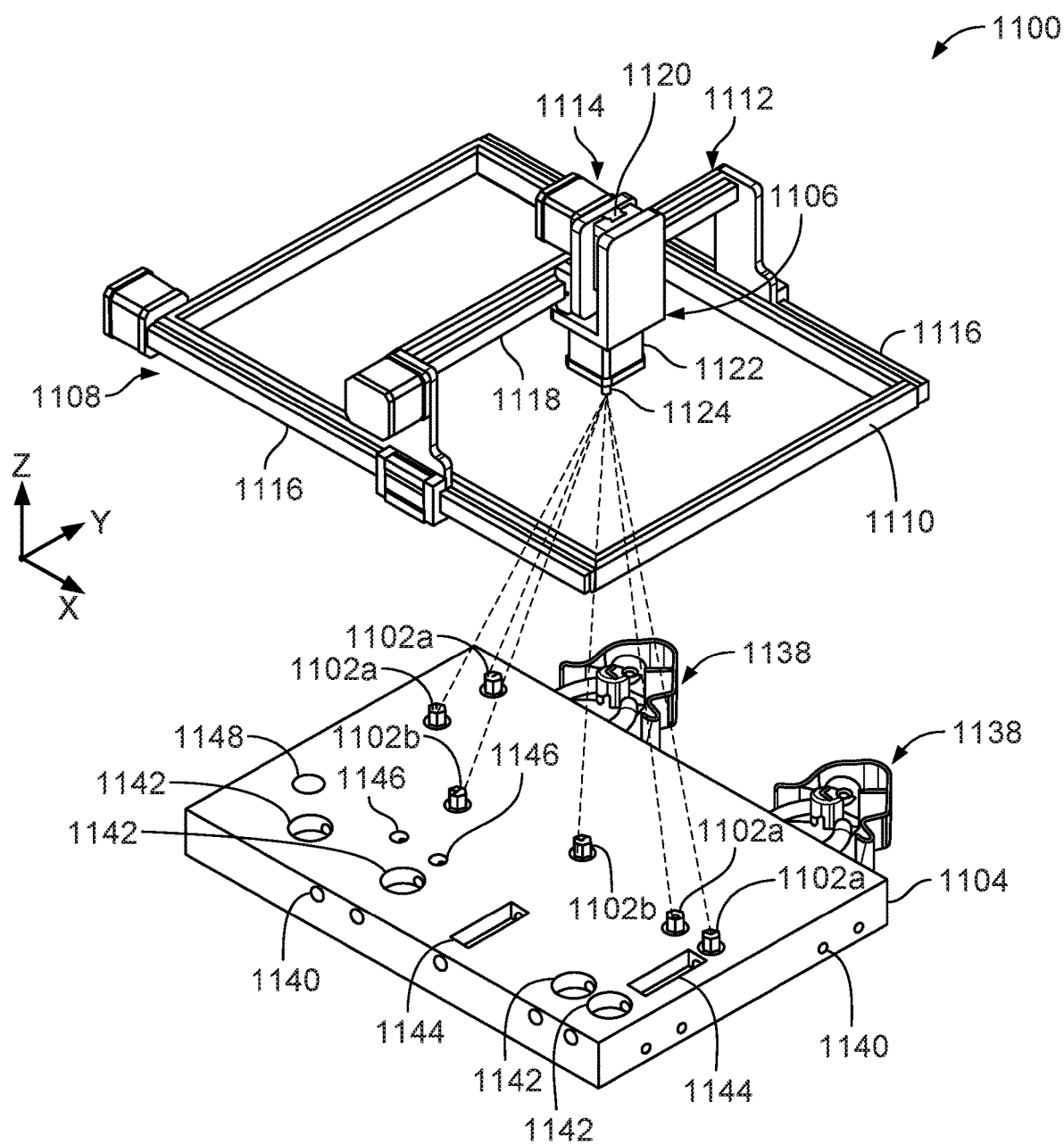
FIG. 30 is an exploded perspective view of the actuation system of FIG. 26.
Figure 42:
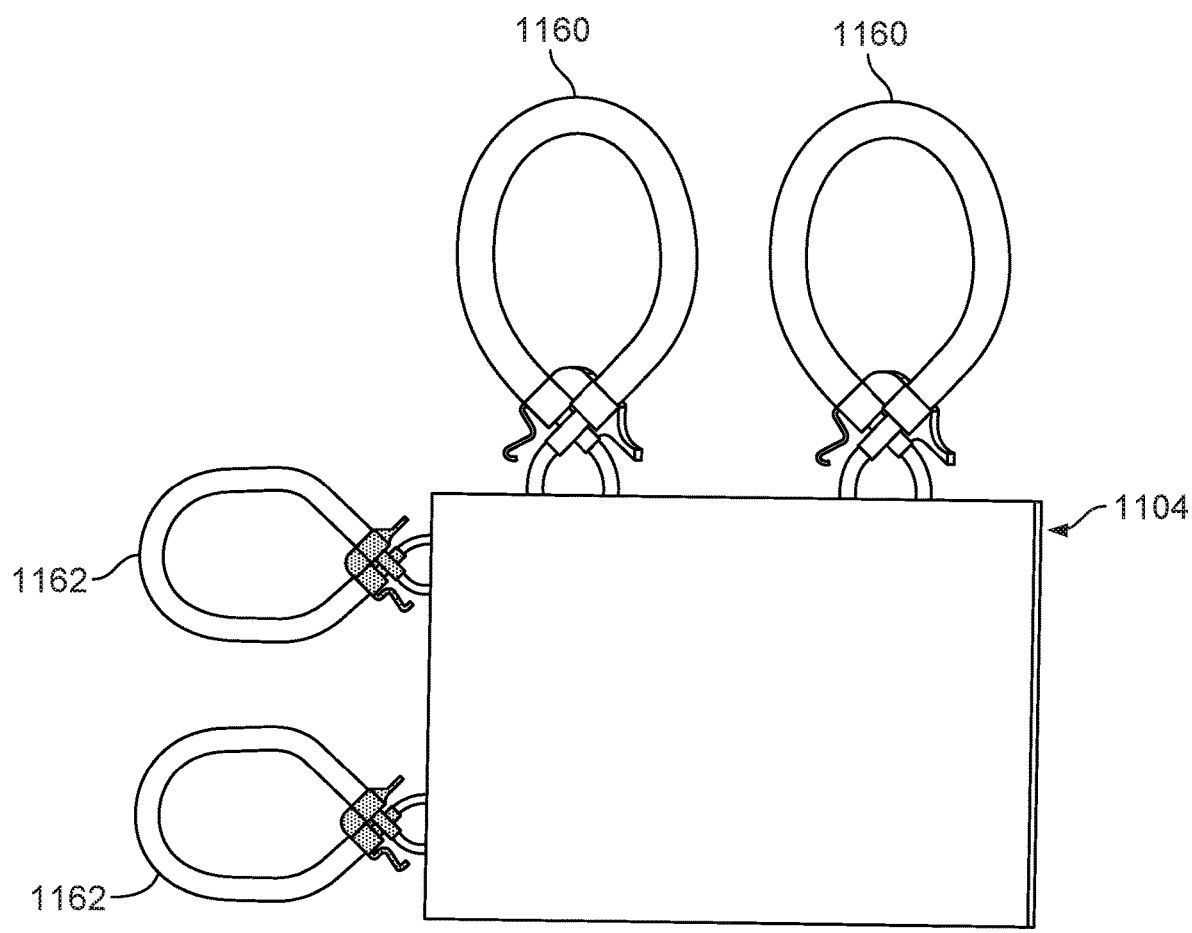
FIG. 42 is a top view of a cassette of FIG. 26, including tubing arranged to interface with multiple pumps of a dialysis system, and with certain features omitted.

Referring particularly to FIG. 30, the cassette 1104 includes two fluid hubs 1138 to which tubing 1160, 1162 can be attached and routed to respective pumps of the dialysis system (as shown in FIG. 42). In some embodiments, the tubing 1160, 1162 may provide embodiments of the fluid line segments 206, 207 of the fluid conditioning system 100. The cassette 1104 also defines multiple peripheral fluid path openings 1140 at which tubing can be secured to the cassette 1104 and multiple recesses 1142, 1144, 1146, 1148 at which various components of the dialysis system (e.g., pressure transducers, optical sensor, and temperature sensors, among others) can interface with the cassette 1104.

Figure 34:
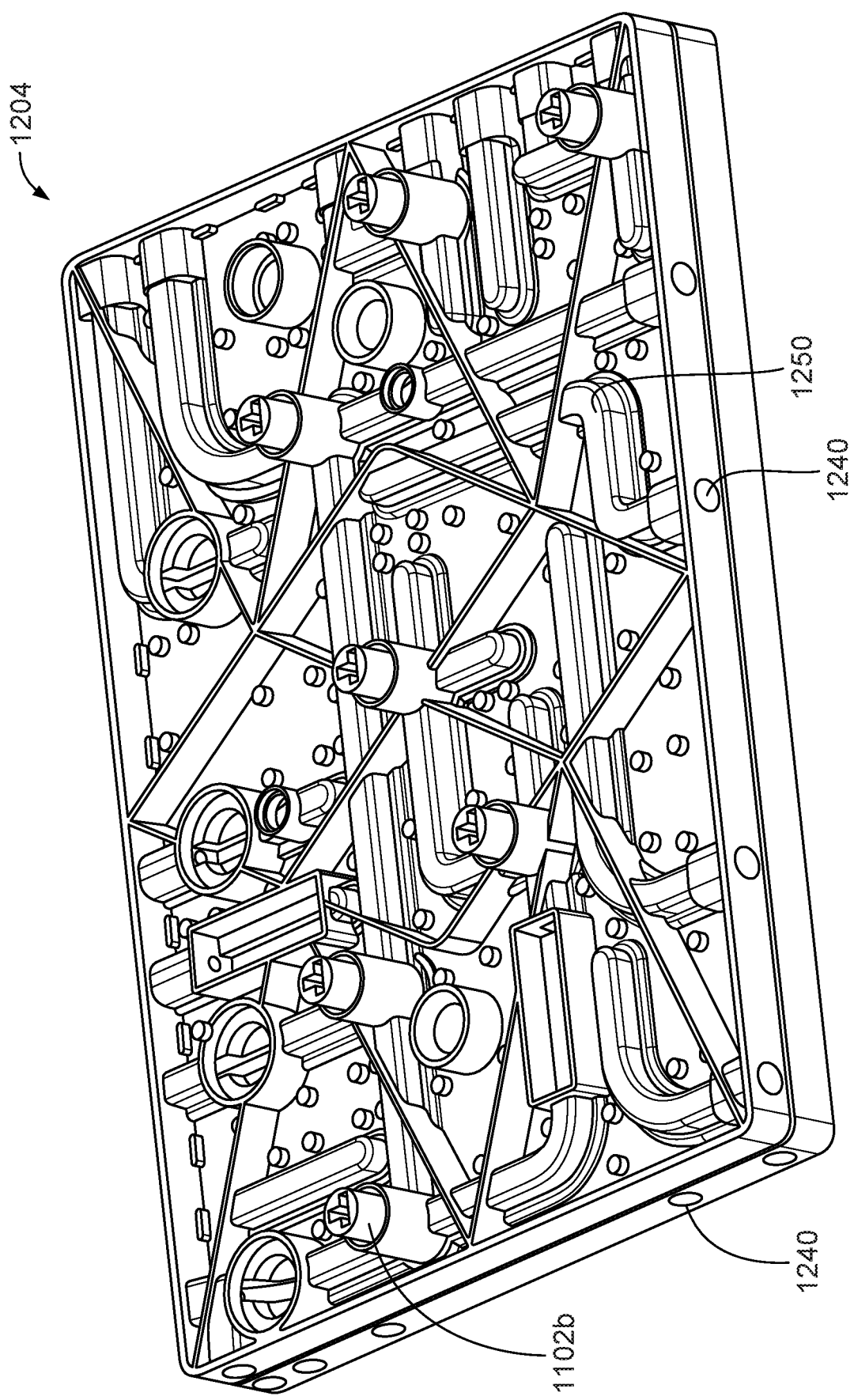
FIG. 34 is a top perspective view of a cassette including multiple valves that can be controlled by the actuation system of FIG. 26.
Figure 35:
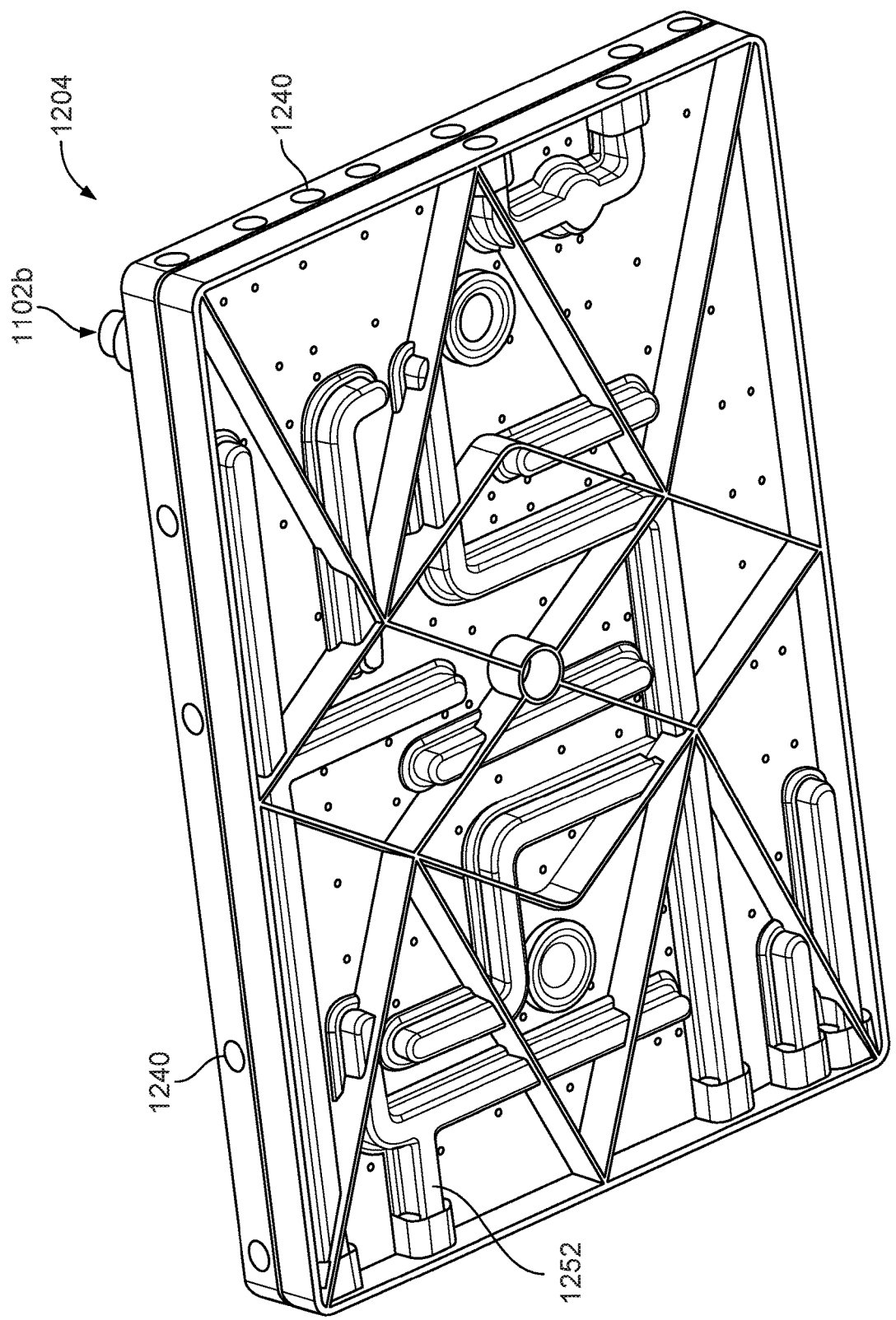
FIG. 35 is a bottom perspective view of the cassette of FIG. 34.
Figure 37:
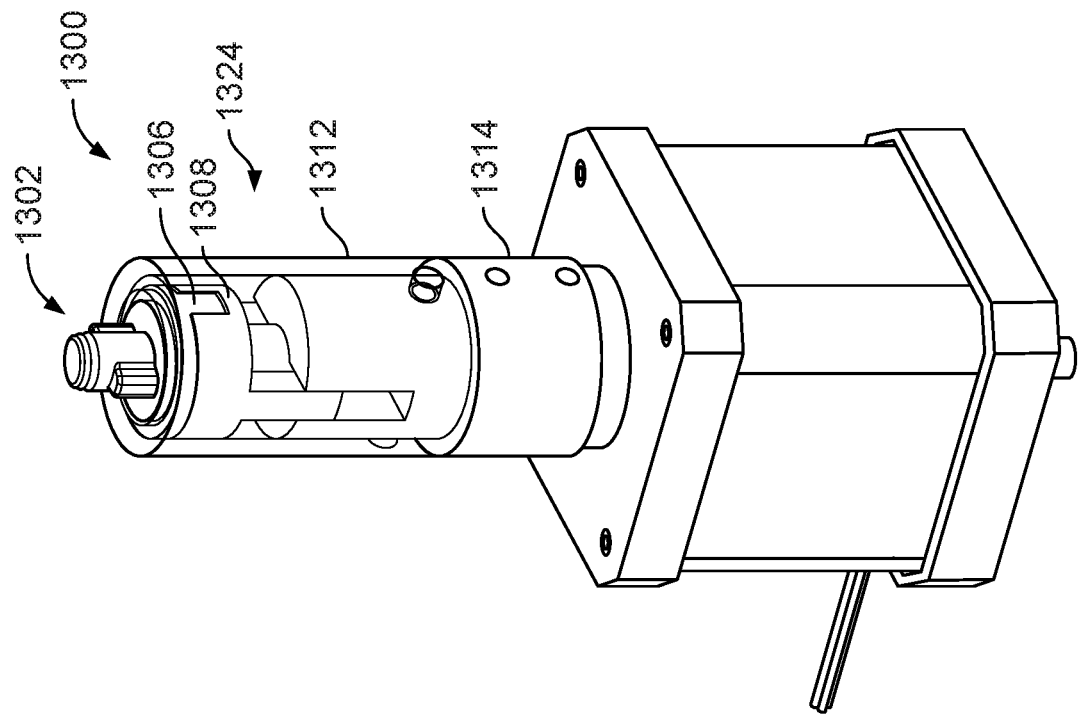
FIG. 37 is a perspective view of the valve drive assembly of FIG. 36, including the outer sleeve.
Figure 36:
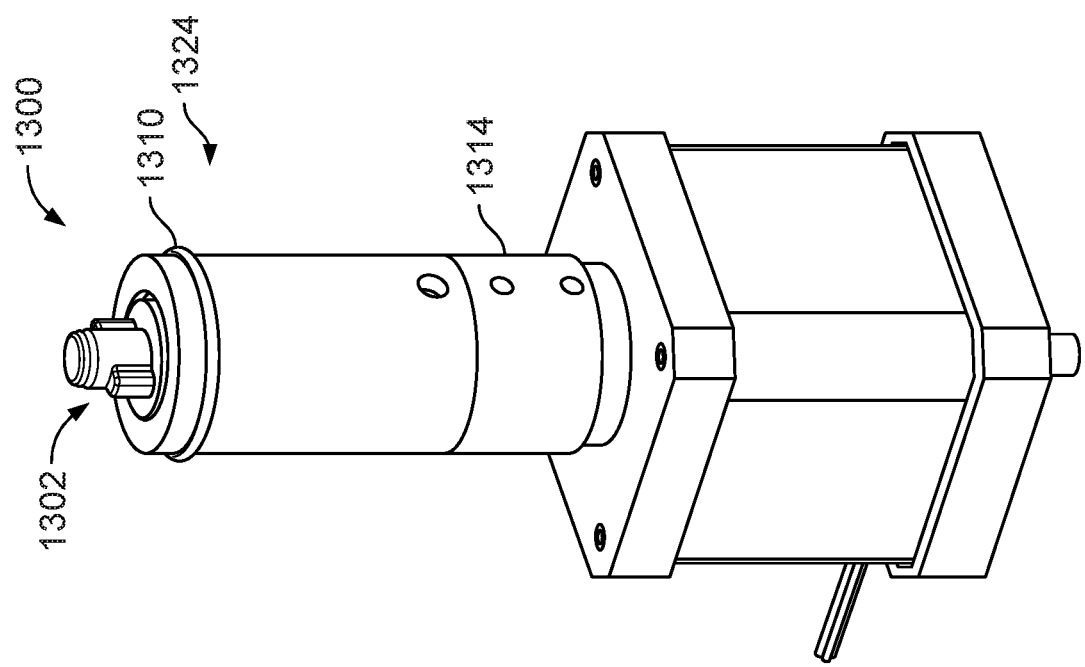
FIG. 36 is a perspective view of a valve drive assembly, with an outer sleeve omitted to illustrate certain internal components.
Figure 39:
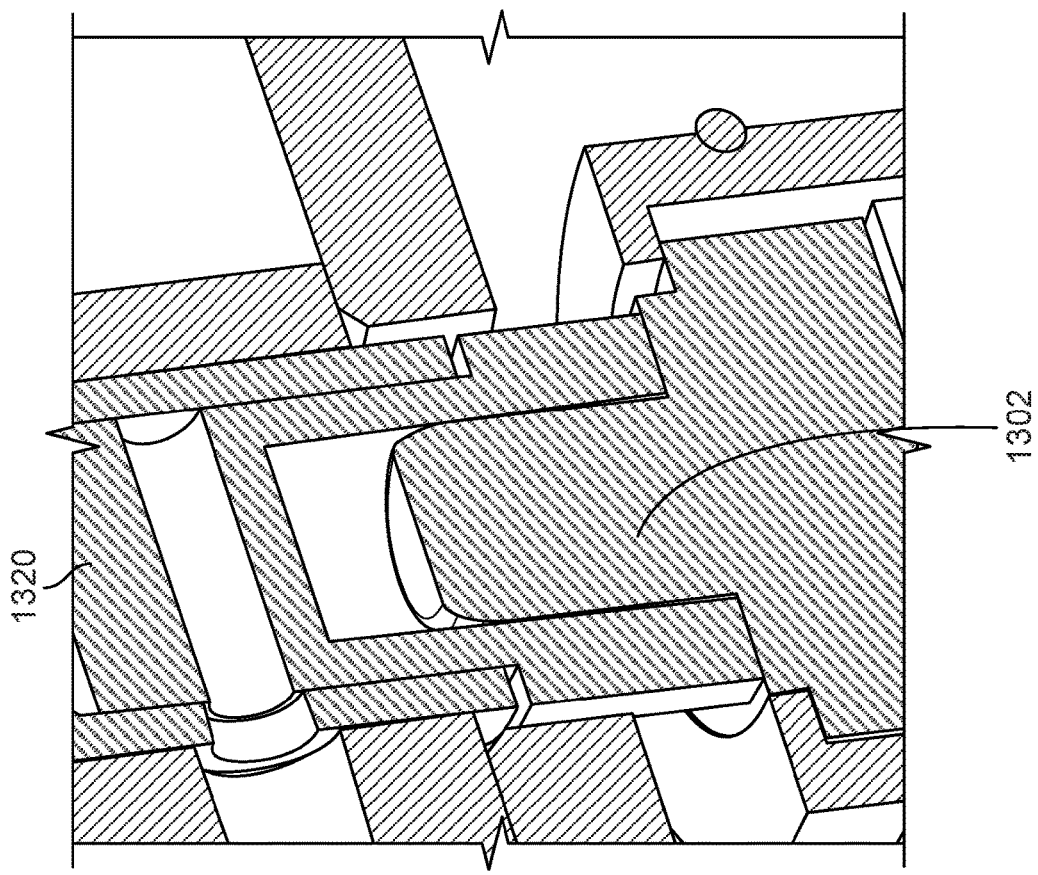
FIG. 39 is a perspective cross-sectional view of a portion of the valve drive assembly of FIG. 36.
Figure 38:
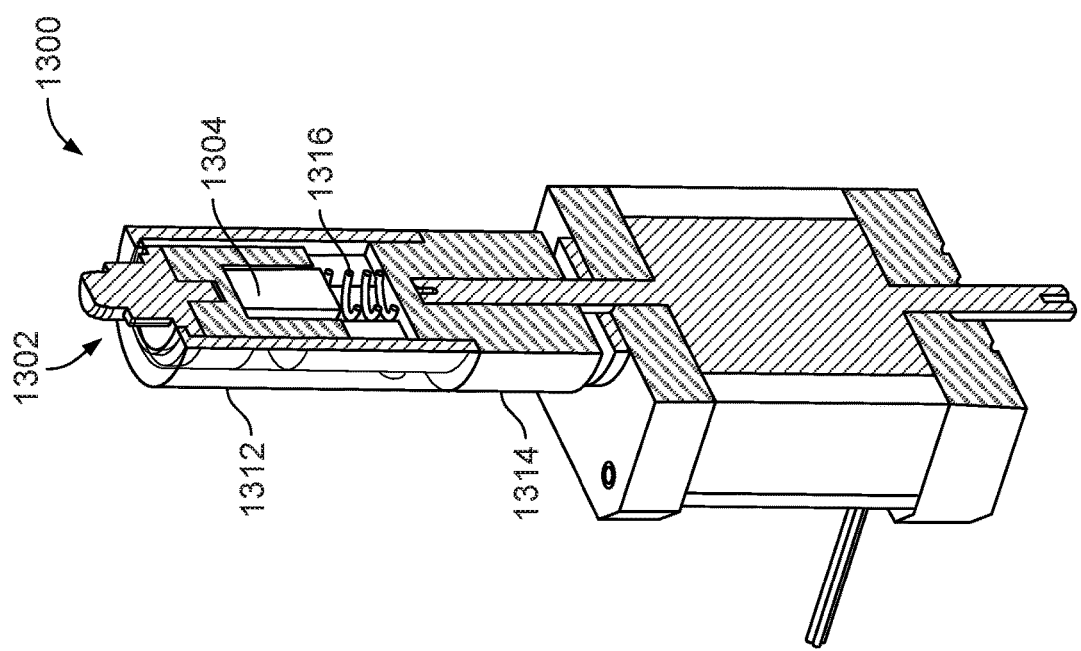
FIG. 38 is a perspective cross-sectional view of the valve drive assembly of FIG. 36.
Figure 41:
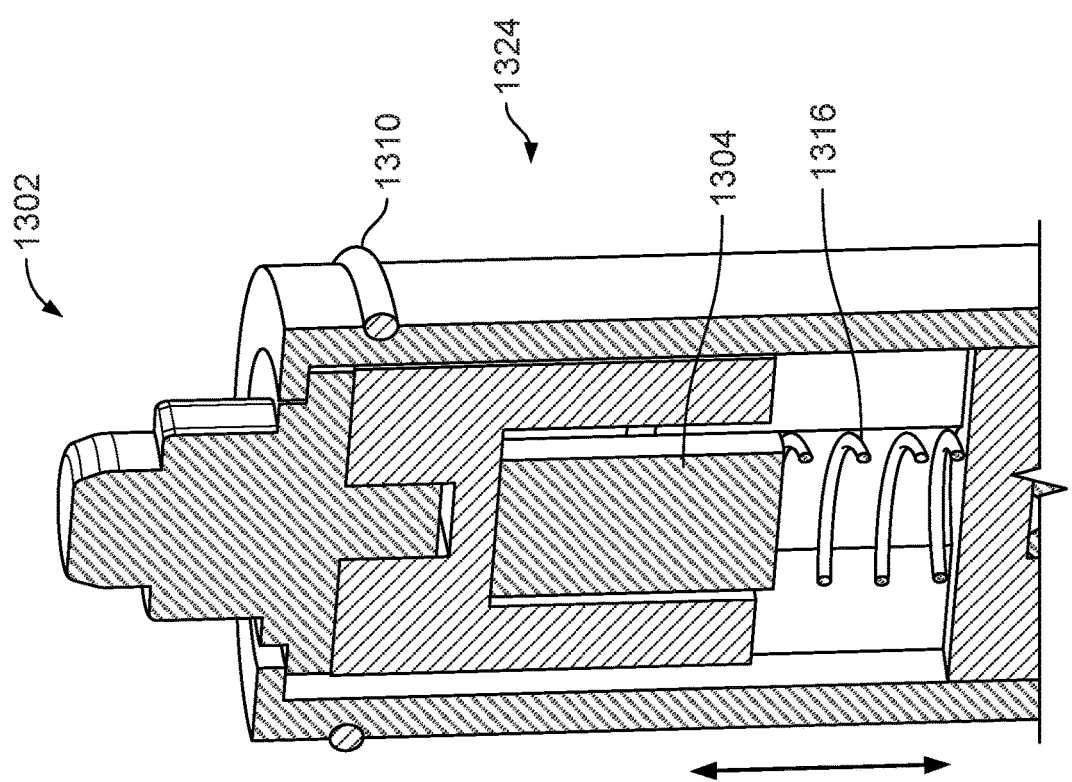
FIG. 41 is a perspective view of a floating z motor drive of the valve drive assembly of FIG. 36.
Figure 40:
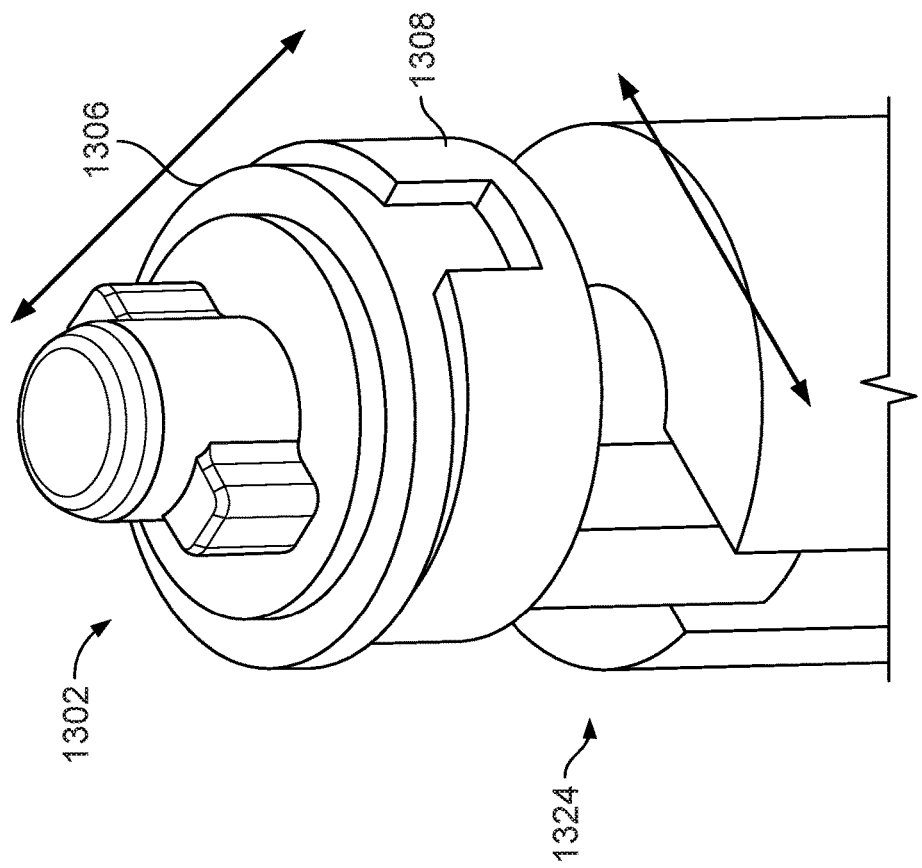
FIG. 40 is a perspective view of a floating x/y motor drive of the valve drive assembly of FIG. 36.

FIGS. 34 and 35 illustrate an alternative embodiment of a cassette 1204 that can be acted upon by the actuation system 1100. The cassette 1204 is similar in structure and function to the cassette 1104, except that the cassette 1204 includes a different number and arrangement of valves 1102 (e.g., seven valves 1102b), corresponding fluid paths 1250, 1252 along which the valves 1102b are positioned, and corresponding peripheral fluid path openings 1240.

In some implementations, results that can be achieved by actuating the valves 1102 of the cassettes 1104, 1204 include providing water to dry-chemistry bags (e.g., the bags 306, 307, 309 of the fluid conditioning system 100) for mixing, providing a flow of dialysate to a patient, opening a flow path to a sorbent cartridge (e.g., the sorbent cartridge 303 of the fluid conditioning system 100), or closing a flow path for heating.

Owing to a capability of the actuation system 100 to control multiple (e.g., all) valves 1102 of a cassette, a design of the dialysis system including the actuation system 1100 can be simplified (e.g., including fewer components and requiring fewer control algorithms) relative to conventional dialysis systems that require a dedicated mechanism for actuating each valve of a cassette.

In some embodiments, an actuator can mate with a valve according to an operation of an encoder or an absolute encoder and with a position stored in memory. For example, Referring to FIGS. 36-41, at initialization of the dialysis system when an interface of a valve 1320 can be assumed known, an actuator 1324 of a valve drive assembly 1300 would move to each valve 1320 and adjust the valve position to a known "initialized" state. A connector interface 1302 utilizes a keyed contact structure that incorporates a spring-loaded axial shaft 1304 (spring-loaded in the z-direction by a spring 1316) that can locate a unique interface connection, such as a key 1128.

The actuator 1324 is rotatable and includes an outer sleeve 1312 that surrounds an x-floating valve socket 1306 and ay-floating valve socket 1308. A seal 1310 of the actuator 1324 seals against a top cover of a cassette. The actuator 1324 also includes a motor attachment piece 1314. A lead-in profile of the actuator 1324 can move the socket into alignment, thereby allowing a motor to clock turning ribs until the socket springs up into the valve 1320. The shaft 1304 can accommodate x/y variation via a unique coupling (e.g., an oldham coupling) and can counteract off-center loads that could cause binding with downward loads, such that the shaft 1304 can stabilize the valve socket.

A number of embodiments have been described in detail above. However, various modifications to these embodiments may be made without departing from the spirit and scope of the above disclosures.

For example, while the actuation system 1100 and the cassettes 1104, 1204 (e.g., including the valves 1102) have been described and illustrated as including certain arrangements and configurations, in some embodiments, actuation systems and cassettes that are otherwise similar in structure and function to the actuation system 1100 or the cassettes 1104, 1204 may include different arrangements or configurations.

For example, while the cassettes 1104, 1204 and the actuation system 1100 have been described and illustrated with respect to rotary valves, in some embodiments, an actuation system that is otherwise similar in function to the actuation system 1100 may be designed to operate on other types of valves within a dialysis fluid cassette, such as push pull valves, pinch valves, or sliding valves, among others.

While the actuation system 1100 has been described and illustrated as being arranged above the cassettes 1104, 1204, in some embodiments, an actuation system that is otherwise similar in structure and function to the actuation system 1100 may be arranged underneath a cassette for selectively actuating valves of the cassette. For example, in some embodiments, such actuation system may be assembled with the fluid conditioning system 100 at a location underneath the fluid cassette such that the orientation of the actuation system is flipped upside down with respect to the orientation of the actuation system 1100 as illustrated. In such embodiments, an actuator of the actuation system may be raised to engage the valves of the cassette.

While the cassettes 1104, 1204 have been described and illustrated as including a certain number of two-way valves 1102a and three-way valves 1102b, in some embodiments, a cassette that is otherwise similar in structure and function to the either of the cassettes 1104, 1204 may include different a different total number of valves 1102 or a different combination of a number of two-way valves 1102a and a number three-way valves 1102b, including a set of all two-way valves 1102a and a set of all three-way valves 1102b.

While the actuation system 1100 has been described for use with the fluid conditioning system 100 as part of a larger hemodialysis system, in some embodiments, the actuation system 1100 can be implemented with other types of medical systems, including PD systems, hemofiltration systems, hemodiafiltration systems, apheresis systems, dialysate generation systems, and water purification systems, among others. For example, the actuation system 1100 may be implemented with a PD system to carry out a PD treatment. Such a PD system may be operated such that certain valves 1102 are opened and closed to allow dialysate to be pumped from a dialysate supply bag to a heater bag. After the dialysate in the heater bag is warmed, certain valves 1102 can be opened and closed to pump the warmed dialysate to the patient. The valves 1102 may then be opened and closed to again allow for dialysate to be pumped to the heater bag where the dialysate is warmed. After the dialysate dwells within the patient's peritoneal cavity for a desired period of time, the valves 1102 may be opened and closed in a way to allow the spent dialysate to be pumped from the patient's peritoneal cavity to a drain. Such a process can be repeated several times during a treatment.

Furthermore, while the fluid conditioning system 100 has been described and illustrated as including the pressure transducers 119 (PT1, PT2, PT3, PT4) for regulating pump flow rates, in some embodiments, a fluid conditioning system that is otherwise similar in construction and function to the fluid conditioning system 100 may alternatively include flow meters instead of pressure transducers for regulating pump flow rates. In some embodiments, a fluid conditioning system that is otherwise similar in construction and function to the fluid conditioning system 100 may not include pressure transducers or flow meters and may instead be RPM-controlled based on a detailed knowledge of the system operation to regulate pump flow rates.

While the fluid conditioning system 100 has been described and illustrated as including peristaltic pumps 103, 104 (P1, P2, P3, P4), in some embodiments, a fluid conditioning system that is otherwise similar in construction and function to the fluid conditioning system 100 may alternatively include a different type of pump, such as an impeller pump, a linear displacement pump, positive displacement pump, or a centrifugal pump.

While the fluid conditioning system 100 has been described and illustrated as including one overflow reservoir (e.g., the secondary reservoir 305), in some embodiments, a fluid conditioning system that is otherwise similar in construction and function to the fluid conditioning system 100 may include one or more additional overflow reservoirs. For example, in some embodiments, an additional reservoir may be connected to the fluid circuit 350 upstream of pump P1 or downstream of pump P2. In some embodiments, an additional reservoir may have a capacity different than that of either reservoir 304 or reservoir 305 or may have a zero volume capacity. In some embodiments, a reservoir may be permanently connected to a drain.

While the heater bag 153 has been described and illustrated as being arranged downstream of pump P2 of the fluid conditioning system 100, in some embodiments, a fluid conditioning system that is otherwise similar in construction and function to the fluid conditioning system 100 may include a heater bag or other heating element that is arranged at a different location along the fluid circuit 350 in order to achieve optimal temperature control of fluid flowing through the fluid circuit 350. For example, in some embodiments, a heater bag may be positioned immediately downstream of the sorbent cartridge 303 and may be powered based on signals from temperature sensor T1 to ensure that the temperature of the dialysis fluid is not high enough to damage internal components of the sorbent cartridge 303. In some embodiments, a heater bag may be located along the fluid circuit 350 anywhere between valve V1 and valve V2, as advantageous (e.g., to promote dissolution of the dry chemicals in the supply bags 306, 307, 309).

While the fluid conditioning system 100 has been described as including three-way valves V1-V7, in some embodiments, a fluid conditioning system that is otherwise similar in construction and function to the fluid conditioning system 100 may alternatively include one or more two-way valves to achieve the fluid flow path scenarios discussed above.

While an operation of the fluid conditioning system 100 has been described and illustrated with respect to certain flow rates, fluid volumes, temperatures, pressures, and time periods, in some embodiments, the fluid conditioning system 100 may be operated to carry out a fluid conditioning cycle with one or more different flow rates, fluid volumes, temperatures, pressures, and time periods, while still functioning to adequately condition dialysate for use in a cooperating dialysis system.

Although the example control system 161, the example hardware system 500, and the example software system 600 have been described respectively in FIGS. 23-25, implementations of the subject matter and the functional operations described above can be implemented in other types of digital electronic circuitry, or in computer software, firmware, or hardware, including the structures disclosed in this specification and their structural equivalents, or in combinations of one or more of them.

Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

Other embodiments are also within the scope of the following claims.

What is claimed is:

1. A dialysis machine, comprising:
 a housing defining a cassette compartment configured to releasably receive a fluid cassette; and
 a drive unit contained within the housing and mounted to a platform of an internal frame of the housing and adjacent to the fluid cassette, wherein the internal frame comprises columnar support members that support an upper panel of the housing, the upper panel defining holes that are positioned and sized to receive locating pins for appropriately positioning the fluid cassette with respect to the upper panel, the drive unit comprising an actuator configured to engage and move a plurality of valves disposed within the fluid cassette to selectively open and close each valve of the plurality of valves; and
 a positioning frame contained within the housing and disposed adjacent the cassette compartment and along which the drive unit can be moved linearly to align the actuator with a selected valve of the plurality of valves, wherein the positioning frame comprises:
  a first linear rail oriented parallel to a first axis of a 3D coordinate system and along which the drive unit can be moved,
  a second linear rail oriented parallel to a second axis of the 3D coordinate system and along which the drive unit can be moved, and
  a third linear rail oriented parallel to a third axis of the 3D coordinate system and along which the drive unit can be moved.

2. The dialysis machine of claim 1, wherein the drive unit is carried by the positioning frame.

3. The dialysis machine of claim 1, wherein the actuator is formed to mate with a complementary feature of each of the plurality of valves.

4. The dialysis machine of claim 1, wherein the actuator is configured to be controlled to apply a force to each valve of the plurality of valves to rotate each valve of the plurality of valves.

5. The dialysis machine of claim 4, wherein the actuator is configured to open and close each valve of the plurality of valves.

6. The dialysis machine of claim 4, wherein the force is a rotational force.

7. The dialysis machine of claim 1, wherein the drive unit is configured to traverse the first, second, and third linear rails in a total time of up to about 0.5 seconds to about 2.0 seconds.

8. The dialysis machine of claim 1, wherein the actuator is configured to open the selected valve to allow fluid to pass through the selected valve.

9. The dialysis machine of claim 1, wherein the actuator is configured to close the selected valve to prevent fluid from passing through the selected valve.

10. The dialysis machine of claim 1, wherein the cassette is a single-use cassette that includes a casing, multiple fluid pathways arranged within the casing, and multiple valves positioned along the fluid pathways.

11. A dialysis system, comprising:
 a fluid cassette carrying a plurality of valves; and
 a dialysis machine, comprising:
  a housing defining a cassette compartment configured to releasably receive the fluid cassette;
  a valve actuation system contained within the housing, mounted to a platform of an internal frame of the housing, and adjacent to the fluid cassette when the fluid cassette is disposed in the cassette compartment, wherein the internal frame comprises columnar support members that support an upper panel of the housing, the upper panel defining holes that are positioned and sized to receive locating pins for appropriately positioning the fluid cassette with respect to the upper panel, the valve actuation system comprising:
   a drive unit comprising an actuator configured to engage and move the plurality of valves disposed within the fluid cassette when the fluid cassette is disposed in the cassette compartment to selectively open and close each valve of the plurality of valves, and
   a positioning frame disposed adjacent the cassette compartment and along which the drive unit can be moved linearly to align the actuator with a selected valve of the plurality of valves, wherein the positioning frame comprises:
    a first linear rail oriented parallel to a first axis of a 3D coordinate system and along which the drive unit can be moved,
    a second linear rail oriented parallel to a second axis of the 3D coordinate system and along which the drive unit can be moved, and
    a third linear rail oriented parallel to a third axis of the 3D coordinate system and along which the drive unit can be moved; and
  a control unit configured to control movements of the valve actuation system.

12. The dialysis system of claim 11, wherein the drive unit is carried by the positioning frame.

13. The dialysis system of claim 11, wherein the actuator is formed to mate with a complementary feature of each of the plurality of valves.

14. The dialysis system of claim 11, wherein the actuator is configured to be controlled to apply a force to each valve of the plurality of valves to rotate each valve of the plurality of valves.

15. The dialysis system of claim 14, wherein the actuator is configured to open and close each valve of the plurality of valves.

16. The dialysis system of claim 14, wherein the force is a rotational force.

17. The dialysis system of claim 11, wherein the drive unit is configured to traverse the first, second, and third linear rails in a total time of up to about 0.5 seconds to about 2.0 seconds.

18. The dialysis system of claim 11, wherein the actuator is configured to open the selected valve to allow fluid to pass through the selected valve.

19. The dialysis system of claim 11, wherein the actuator is configured to close the selected valve to prevent fluid from passing through the selected valve.

20. The dialysis system of claim 11, further comprising at least one of: a prime tank for collecting water to produce dialysate, a sorbent cartridge for filtering tap water to provide purified water suitable for creating dialysate and for cleansing dialysate exiting the dialysis system, a primary reservoir for collecting fluid exiting the sorbent cartridge, a secondary reservoir for collecting fluid that exceeds a capacity of the primary reservoir, a bag for containing an electrolyte solution, a bag for containing a salt-dextrose solution, a bag for containing dilution water, and a bag for containing a bicarbonate solution.

* * * * *